US012788849B2

(12) United States Patent
Dufrane

(10) Patent No.: US 12,788,849 B2
(45) Date of Patent: Nov. 10, 2026

(54) BIOMATERIAL COMPRISING ADIPOSE-DERIVED STEM CELLS AND GELATIN AND METHOD FOR PRODUCING THE SAME

(71) Applicant: NOVADIP BIOSCIENCES, Mont-Saint-Guibert (BE)

(72) Inventor: Denis Dufrane, Lasne (BE)

(73) Assignee: NOVADIP BIOSCIENCES, Mont-Saint-Guibert (BE)

( * ) Notice: Subject to any disclaimer, the term of this patent is extended or adjusted under 35 U.S.C. 154(b) by 552 days.

(21) Appl. No.: 17/273,143

(22) PCT Filed: Sep. 20, 2019

(86) PCT No.: PCT/EP2019/075413
§ 371 (c)(1),
(2) Date: Mar. 3, 2021

(87) PCT Pub. No.: WO2020/058511
PCT Pub. Date: Mar. 26, 2020

(65) Prior Publication Data

US 2021/0322644 A1 Oct. 21, 2021

Related U.S. Application Data

(60) Provisional application No. 62/734,064, filed on Sep. 20, 2018.

(51) Int. Cl.

| | |
|---|---|
| ***A61P 17/02*** | (2006.01) |
| ***A61L 27/22*** | (2006.01) |
| ***A61L 27/36*** | (2006.01) |
| ***A61L 27/38*** | (2006.01) |
| ***C12N 5/0775*** | (2010.01) |

(52) U.S. Cl.
CPC ......... *A61L 27/3834* (2013.01); *A61L 27/222* (2013.01); *A61L 27/3633* (2013.01); *A61P 17/02* (2018.01); *C12N 5/0667* (2013.01); *A61L 2430/34* (2013.01); *C12N 2506/1384* (2013.01); *C12N 2513/00* (2013.01)

(58) Field of Classification Search
CPC ............... A61L 27/3834; A61L 27/222; A61L 27/3633; A61L 2430/34; A61L 2400/12; A61L 27/3804; A61P 17/02; C12N 5/0667; C12N 2506/1384; C12N 2513/00; C12N 2533/54; C12N 5/0654; C12N 5/0697; C12N 2533/90; A61K 9/70; A61K 35/35; A61K 35/28
See application file for complete search history.

(56) References Cited

U.S. PATENT DOCUMENTS

| | | | | |
|---|---|---|---|---|
| 2008/0085322 | A1* | 4/2008 | Xu | A61K 36/899 514/460 |
| 2015/0081033 | A1* | 3/2015 | Yoshikawa | A61L 27/3834 623/23.51 |
| 2016/0256499 | A1* | 9/2016 | Peltz | A61K 35/407 |
| 2018/0371416 | A1* | 12/2018 | Alsberg | C12N 5/0655 |

OTHER PUBLICATIONS

Lewis et al (Journal of Investigative Surgery, 26, 141-148, 2013, DOI: 10.3109/08941939.2012.724519, Published online: Mar. 20, 2013). (Year: 2013).*
Fang et al (Annals of Plastic Surgery & vol. 73, No. 5, Nov. 2014, DOI: 10.1097/SAP.0b013e3182840883) (Year: 2014).*
Yu et al (Biomaterials 120 (2017) 66-80, http://dx.doi.org/10.1016/j.biomaterials.2016.12.017, Available online Dec. 23, 2016) ( Year: 2016).*
Das et al (Rev Neurosci . Nov. 26, 2019;30(8):839-855. doi: 10.1515/revneuro-2019-0002.) (Year: 2019).*
Borlongan, 2019 (Stem Cells Translational Medicine 2019;8:983-988, http://dx.doi.org/10.1002/sctm.19-0076) (Year: 2019).*
Yu et al(Front. Cell Dev. Biol. 10:812262., 2022, doi: 10.3389/fcell.2022.812262) (Year: 2022).*
Caplan et al (Front. Immunol. 10:1645, doi: 10.3389/fimmu.2019.01645, published Jul. 31, 2019) (Year: 2019).*
Loupy et al (Lancet 2023; 402: 1158-69, Doi: /10.1016/ S0140-6736(23)01349-1) (Year: 2023).*
Liu et al., 2017 (Front. Immunol. 8:645., p. 1-6, Doi: 10.3389/fimmu.2017.00645) (Year: 2017).*

* cited by examiner

*Primary Examiner* — Peter Paras, Jr.
*Assistant Examiner* — Khoa Nhat Tran
(74) *Attorney, Agent, or Firm* — Jerold I. Schneider; SCHNEIDER IP LAW

(57) ABSTRACT

The present invention relates to a biomaterial comprising adipose-derived stem cells (ASCs), an extracellular matrix and gelatin. The present invention also relates to methods for producing the biomaterial and uses thereof.

5 Claims, 18 Drawing Sheets

A

B

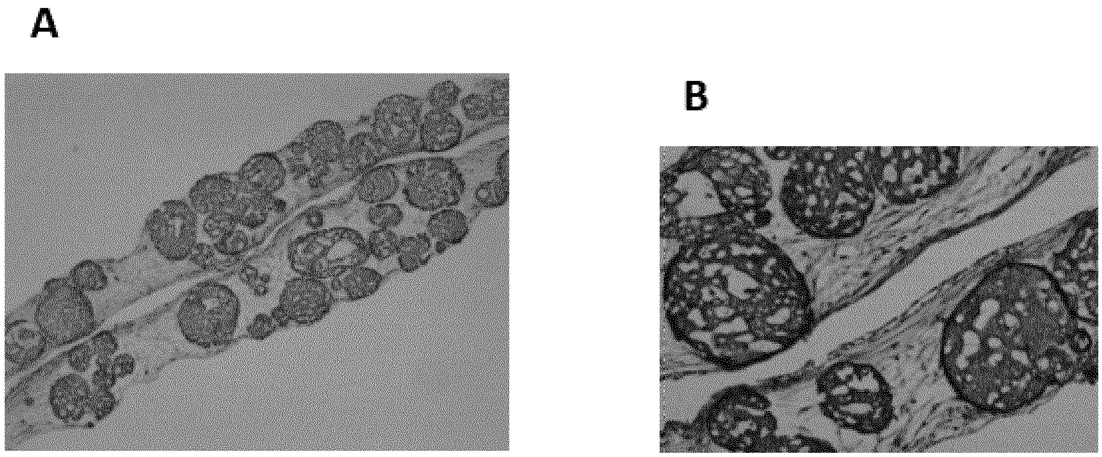
FIG. 2A-B
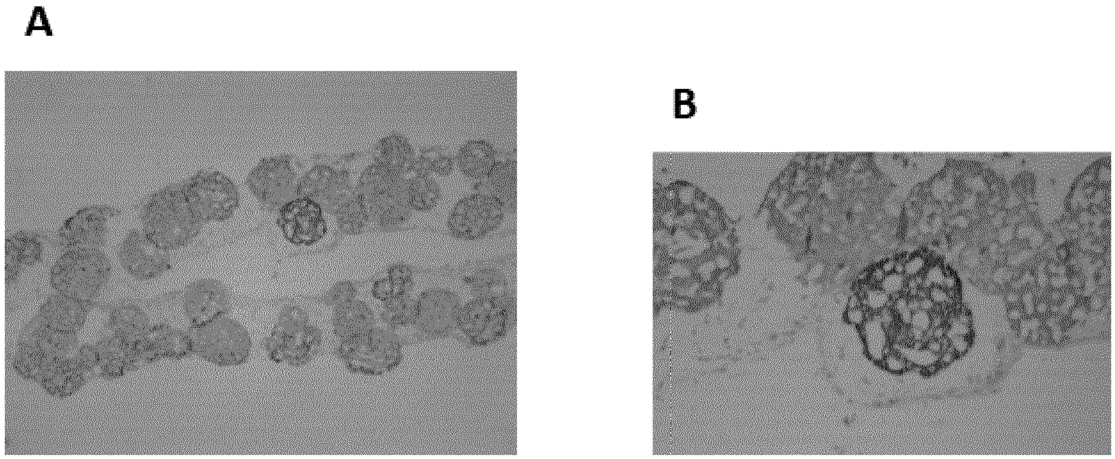
FIG. 3A-B
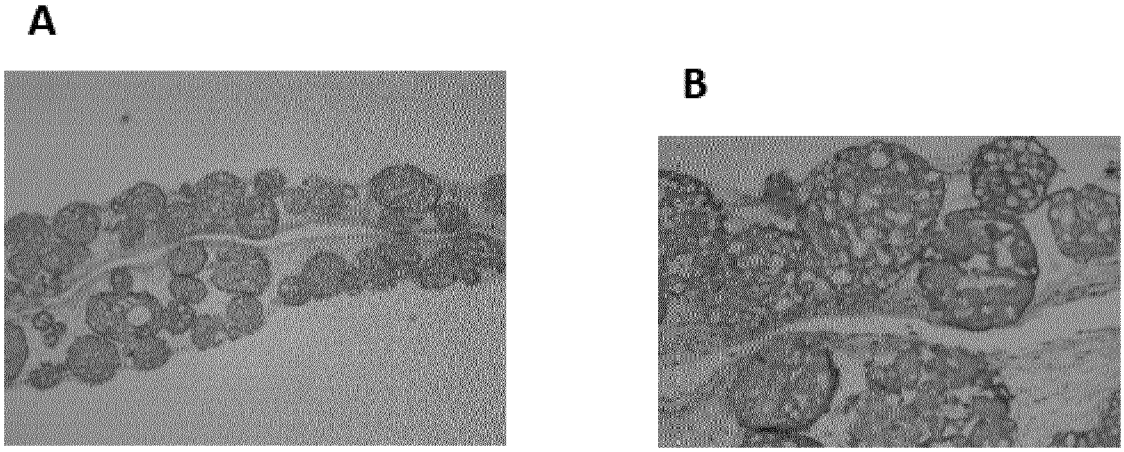
FIG. 4A-B

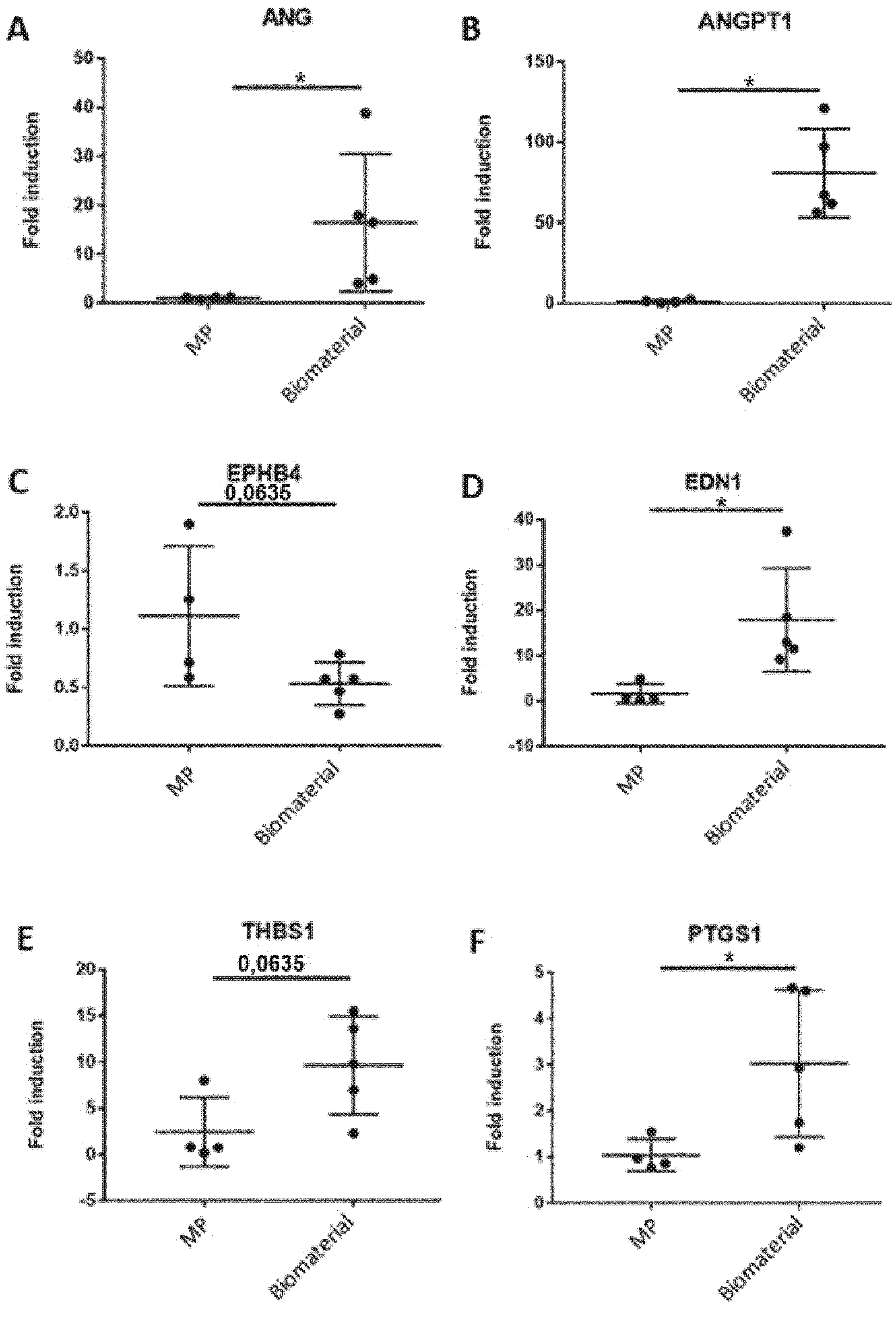
FIG. 5A-F

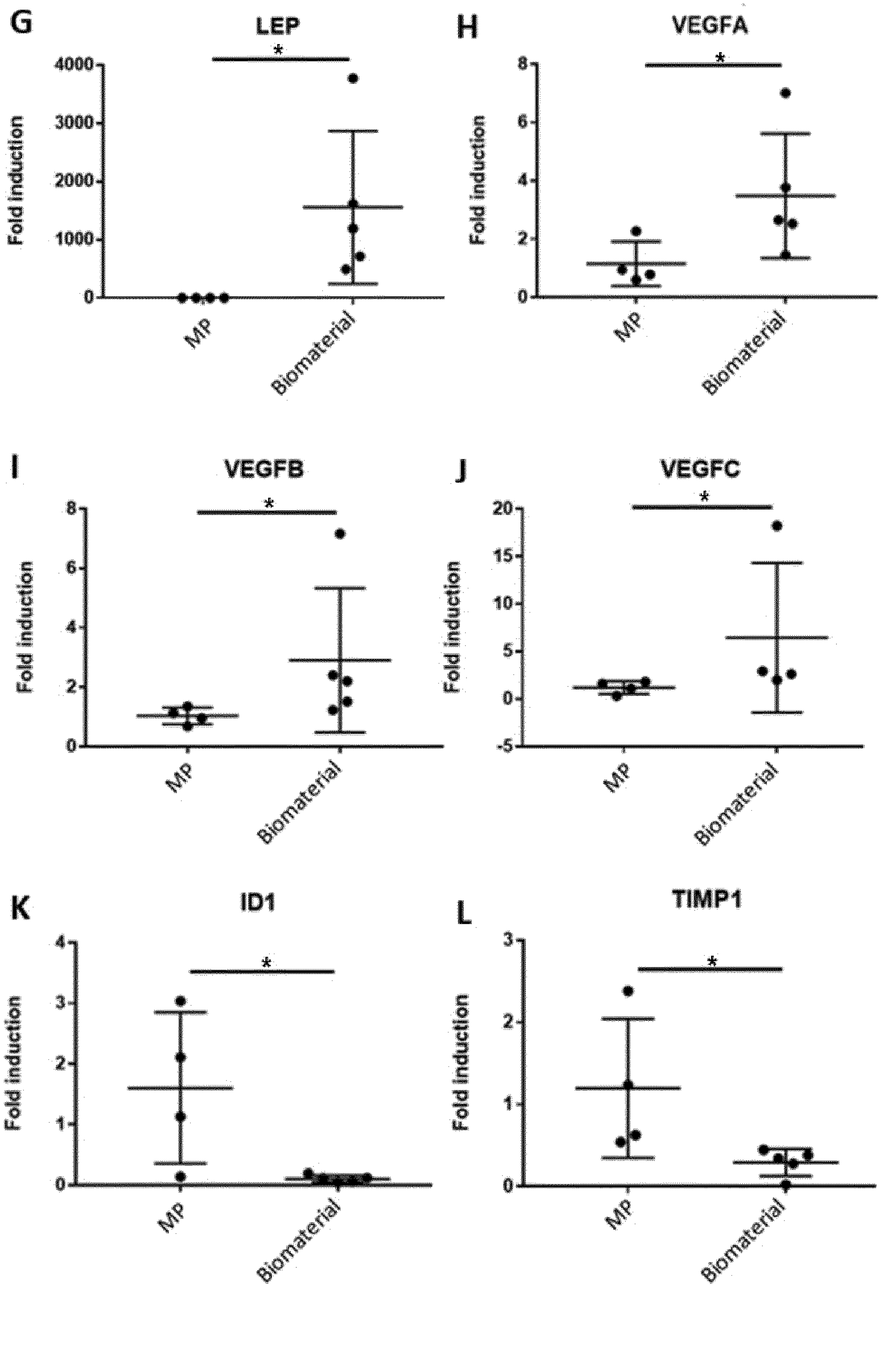
FIG. 5G-L

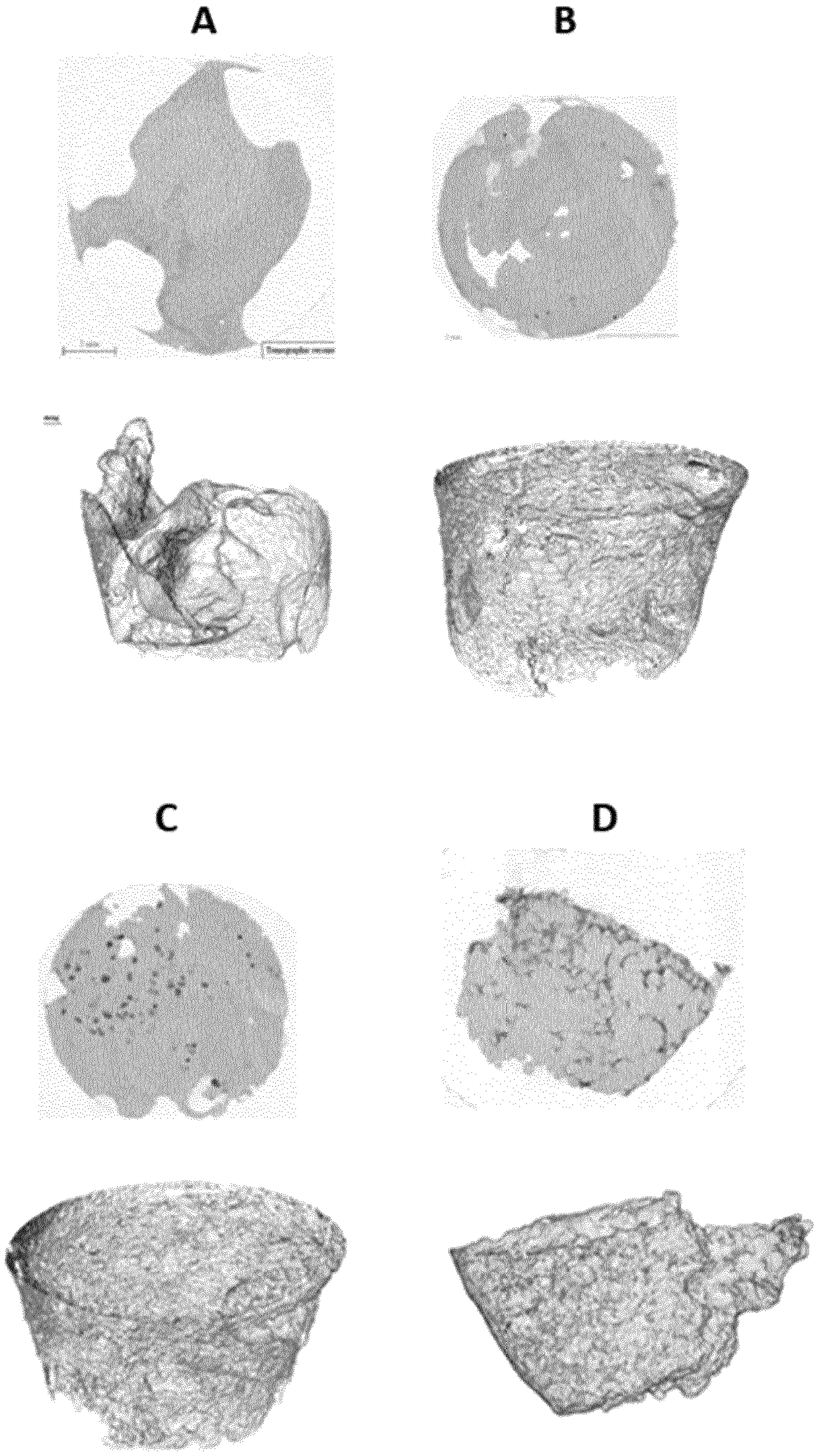
FIG. 6A-D

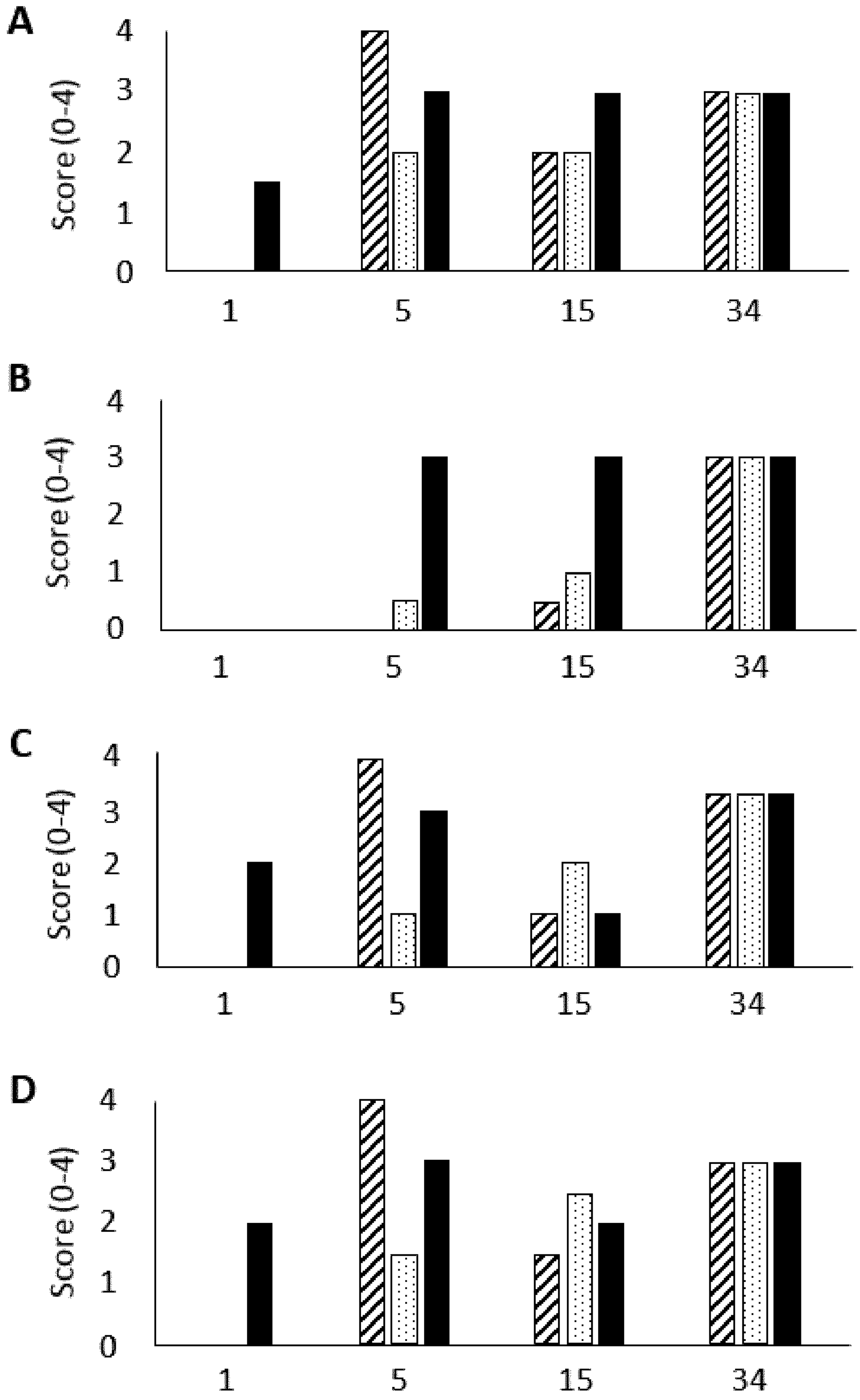
FIG. 19A-D

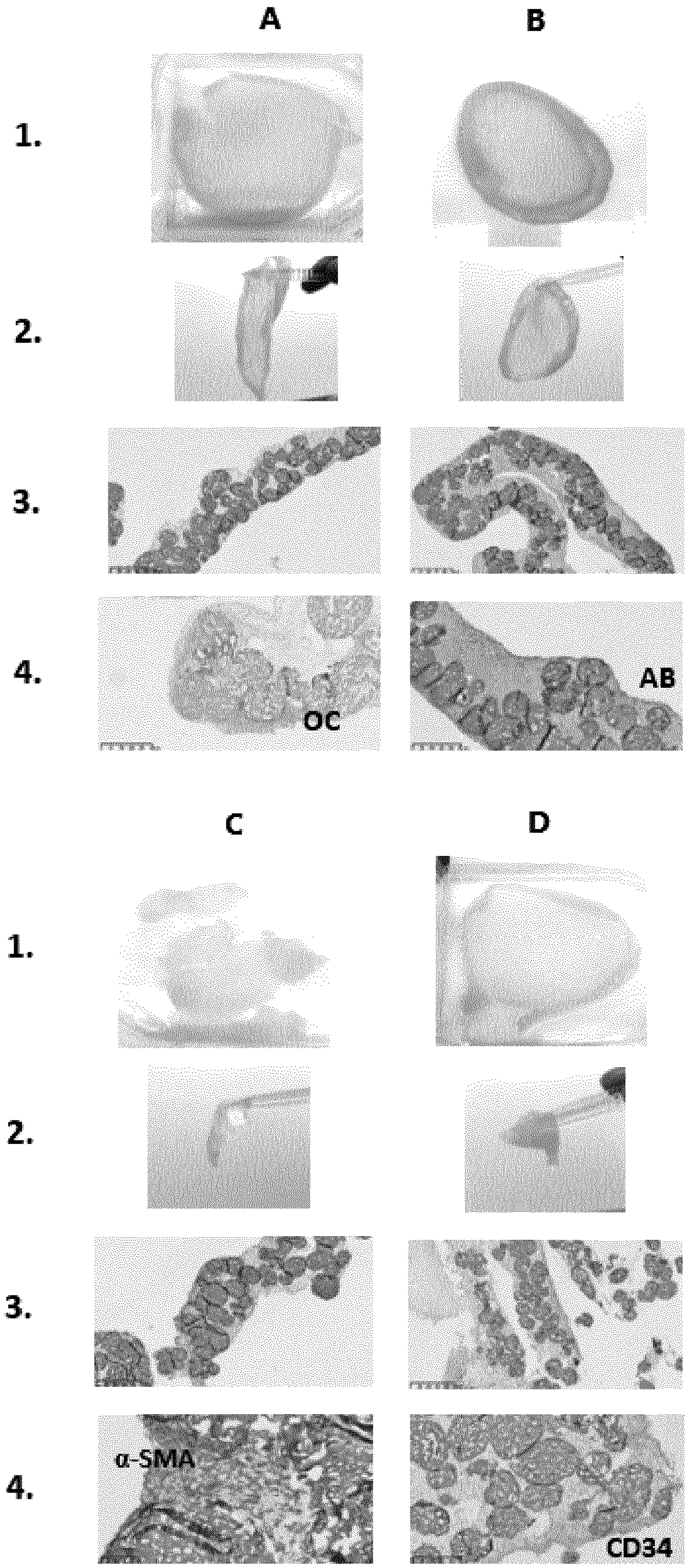
FIG. 20A-D

BIOMATERIAL COMPRISING ADIPOSE-DERIVED STEM CELLS AND GELATIN AND METHOD FOR PRODUCING THE SAME

RELATED APPLICATIONS

This application is a 35 U.S.C. § 371 filing of International Patent Application No. PCT/EP2019/075413, filed Sep. 20, 2019, which claims priority to U.S. Provisional Patent Application Ser. No. 62/734,064, filed Sep. 20, 2018, the entire disclosures of which are hereby incorporated herein by reference.

FIELD OF INVENTION

The present invention relates to the field of stem cells and their use for the production of multi-dimensional biomaterials. In particular, the present invention relates to biomaterials comprising adipose-derived stem cells (ASCs), methods for preparing and using such biomaterials for therapy.

BACKGROUND OF INVENTION

Tissue engineering involves the restoration of tissue structure or function through the use of living cells. The general process consists of cell isolation and proliferation, followed by a re-implantation procedure in which a scaffold material is used. Mesenchymal stem cells provide a good alternative to cells from mature tissue and have a number of advantages as a cell source for bone and cartilage tissue regeneration for example.

By definition, a stem cell is characterized by its ability to undergo self-renewal and its ability to undergo multilineage differentiation and form terminally differentiated cells. Ideally, a stem cell for regenerative medicinal applications should meet the following set of criteria: (i) should be found in abundant quantities (millions to billions of cells); (ii) can be collected and harvested by a minimally invasive procedure; (iii) can be differentiated along multiple cell lineage pathways in a reproducible manner; (iv) can be safely and effectively transplanted to either an autologous or allogeneic host.

Studies have demonstrated that stem cells have the capacity to differentiate into cells of mesodermal, endodermal and ectodermal origins. The plasticity of MSCs most often refers to the inherent ability retained within stem cells to cross lineage barriers and to adopt the phenotypic, biochemical and functional properties of cells unique to other tissues. Adult mesenchymal stem cells can be isolated from bone marrow and adipose tissue, for example.

Adipose-derived stem cells are multipotent and have profound regenerative capacities. The following terms have been used to identify the same adipose tissue cell population: Adipose-derived Stem/Stromal Cells (ASCs); Adipose Derived Adult Stem (ADAS) Cells, Adipose Derived Adult Stromal Cells, Adipose Derived Stromal Cells (ADSC), Adipose Stromal Cells (ASC), Adipose Mesenchymal Stem Cells (AdMSC), Lipoblasts, Pericytes, Pre-Adipocytes, Processed Lipoaspirate (PLA) Cells. The use of this diverse nomenclature has led to significant confusion in the literature. To address this issue, the International Fat Applied Technology Society reached a consensus to adopt the term "Adipose-derived Stem Cells" (ASCs) to identify the isolated, plastic-adherent, multipotent cell population.

Tissue reconstruction encompasses bone and cartilage reconstruction, but also dermis, epidermis and muscle reconstruction. Currently, each tissue defect should be treated with a specific treatment, requiring a different development for each.

There is thus still a need in the art for tissue engineered materials for tissue reconstruction and/or regeneration that are fully biocompatible and provide appropriate mechanical features for the designated applications, although usable on a broad range of tissues. Therefore, the present invention relates to a graft made of ASCs differentiated in a multi-dimensional structure with gelatin.

SUMMARY

The present invention relates to a biomaterial having a multi-dimensional structure comprising differentiated adipose-derived stem cells (ASCs), an extracellular matrix and gelatin.

In one embodiment, gelatin is porcine gelatin. In one embodiment, gelatin is in form of particles. In one embodiment, gelatin have a mean diameter ranging from about 50 μm to about 1000 μm, preferably from about 75 μm to about 750 μm, more preferably from about 100 μm to about 500 μm.

In one embodiment, the biomaterial is three-dimensional.

In certain embodiments, the biomaterial is moldable or formable.

In one embodiment, the ASCs are differentiated into cells selected from the group comprising or consisting of osteoblasts, chondrocytes, keratinocytes, myofibroblasts, endothelial cells and adipocytes.

The present invention also relates to a medical device or a pharmaceutical composition comprising the multi-dimensional biomaterial as described hereinabove.

Another aspect of the present invention is a method for producing the multi-dimensional biomaterial as described hereinabove comprising the steps of:

adipose-derived stem cells (ASCs) proliferation,

ASCs differentiation at the fourth passage, and multi-dimensional induction, preferably 3D induction.

The present invention further relates to a multi-dimensional biomaterial obtainable by the method as described hereinabove.

Still another object of the present invention is a biomaterial as described hereinabove for use for treating a tissue defect. In one embodiment, the tissue is selected from the group comprising or consisting of bone, cartilage, dermis, epidermis, muscle, endothelium and adipose tissue.

DEFINITIONS

In the present invention, the following terms have the following meanings:

- The term "about" preceding a value means plus or less 10% of the value of said value.
- The term "adipose tissue" refers to any fat tissue. The adipose tissue may be brown or white adipose tissue, derived from subcutaneous, omental/visceral, mammary, gonadal, or other adipose tissue site. Preferably, the adipose tissue is subcutaneous white adipose tissue. Such cells may comprise a primary cell culture or an immortalized cell line. The adipose tissue may be from any organism, living or deceased, having fat tissue. Preferably, the adipose tissue is animal, more preferably mammalian, most preferably the adipose tissue is human. A convenient source of adipose tissue is from liposuction surgery, however, the source of adipose tissue or the method of isolation of adipose tissue is not critical to the invention.

The term "adipose-derived stem cells" as used herein refers to the "non-adipocyte" fraction of adipose tissue. The cells can be fresh, or in culture. "Adipose-derived stem cells" (ASCs) refers to stromal cells that originate from adipose tissue which can serve as precursors to a variety of different cell types such as, but not limited to, adipocytes, osteocytes, chondrocytes.

The term "regeneration" or "tissue regeneration" includes, but is not limited to the growth, generation, or reconstruction of new cells types or tissues from the ASCs of the instant disclosure. In one embodiment, these cells types or tissues include but are not limited to osteogenic cells (e.g. osteoblasts), chondrocytes, endothelial cells, cardiomyocytes, hematopoietic cells, hepatic cells, adipocytes, neuronal cells, and myotubes. In a particular embodiment, the term "regeneration" or "tissue regeneration" refers to generation or reconstruction of osteogenic cells (e.g. osteoblasts) from the ASCs of the instant disclosure.

The term "growth factors" as used herein are molecules which promote tissue growth, cellular proliferation, vascularization, and the like. In a particular embodiment, the term "growth factors" include molecules which promote bone tissue.

The term "cultured" as used herein refers to one or more cells that are undergoing cell division or not undergoing cell division in an in vitro, in vivo, or ex vivo environment. An in vitro environment can be any medium known in the art that is suitable for maintaining cells in vitro, such as suitable liquid media or agar, for example. Specific examples of suitable in vitro environments for cell cultures are described in Culture of Animal Cells: a manual of basic techniques (3rd edition), 1994, R. I. Freshney (ed.), Wiley-Liss, Inc.; Cells: a laboratory manual (vol. 1), 1998, D. L. Spector, R. D. Goldman, L. A. Leinwand (eds.), Cold Spring Harbor Laboratory Press; and Animal Cells: culture and media, 1994, D. C. Darling, S. J. Morgan John Wiley and Sons, Ltd.

The term "confluency" refers to the number of adherent cells in a cell culture surface (such as a culture dish or a flask), i.e. to the proportion of the surface which is covered by cells. A confluency of 100% means the surface is completely covered by the cells. In one embodiment, the expression "cells reach confluence" or "cells are confluent" means that cells cover from 80 to 100% of the surface. In one embodiment, the expression "cells are subconfluent" means that cells covered from 60 to 80% of the surface. In one embodiment, the expression "cells are overconfluent" means that cells cover at least 100% of the surface and/or are 100% confluent since several hours or days.

The term "refrigerating" or "refrigeration" refers to a treatment bringing at temperatures of less than the subject's normal physiological temperature. For example, at one or more temperatures selected in the range of about −196° C. to about +32° C., for extended periods of time, e.g. at least about an hour, at least about a day, at least about a week, at least about 4 weeks, at least about 6 months, etc. In one embodiment, "refrigerating" or "refrigeration" refers to a treatment bringing at temperatures of less than 0° C. The refrigerating may be carried out manually, or preferably carried out using an ad hoc apparatus capable of executing a refrigerating program. In one embodiment, the term "refrigeration" includes the methods known in the art as "freezing" and "cryopreservation". The skilled person will understand that the refrigerating method may include other steps, including the addition of reagents for that purpose.

The term "non-embryonic cell" as used herein refers to a cell that is not isolated from an embryo. Non-embryonic cells can be differentiated or nondifferentiated. Non-embryonic cells can refer to nearly any somatic cell, such as cells isolated from an ex utero animal. These examples are not meant to be limiting.

The term "differentiated cell" as used herein refers to a precursor cell that has developed from an unspecialized phenotype to a specialized phenotype. For example, adipose-derived stem cells can differentiate into osteogenic cells.

The term "differentiation medium" as used herein refers to one of a collection of compounds that are used in culture systems of this invention to produce differentiated cells. No limitation is intended as to the mode of action of the compounds. For example, the agent may assist the differentiation process by inducing or assisting a change in phenotype, promoting growth of cells with a particular phenotype or retarding the growth of others. It may also act as an inhibitor to other factors that may be in the medium or synthesized by the cell population that would otherwise direct differentiation down the pathway to an unwanted cell type.

The terms "treatment", "treating" or "alleviation" refers to therapeutic treatments wherein the object is to prevent or slow down (lessen) the bone defect. Those in need of treatment include those already with the disorder as well as those prone to have the disorder or those in whom the bone defect is to be prevented. A subject is successfully "treated" for a bone defect if, after receiving a therapeutic amount of an biomaterial according to the methods of the present invention, the patient shows observable and/or measurable reduction in or absence of one or more of the following: reduction in the bone defect and/or relief to some extent, one or more of the symptoms associated with the bone defect; reduced morbidity and mortality, and improvement in quality of life issues. The above parameters for assessing successful treatment and improvement in the disease are readily measurable by routine procedures familiar to a physician.

In the context of therapeutic use of the disclosed biomaterials, in 'allogeneic' therapy, the donor and the recipient are different individuals of the same species, whereas in 'autologous' therapy, the donor and the recipient is the same individual, and in 'xenogeneic' therapy, the donor derived from an animal of a different species than the recipient.

The term "effective amount" refers to an amount sufficient to effect beneficial or desired results including clinical results. An effective amount can be administered in one or more administrations.

The term "subject" refers to a mammal, preferably a human. Examples of subjects include humans, non-human primates, dogs, cats, mice, rats, horses, cows and transgenic species thereof. In one embodiment, a subject may be a "patient", i.e. a warm-blooded animal, more preferably a human, who/which is awaiting the receipt of, or is receiving medical care or was/is/will be the object of a medical procedure, or is monitored for the development of a disease. In one embodiment, the subject is an adult (for example a human subject above the age of 18). In another embodiment, the subject is a child (for example a human subject below the age of 18). In one embodiment, the subject is a male. In another embodiment, the subject is a female.

The term "biocompatible" refers to a non-toxic material that is compatible with a biological system such as a cell, cell culture, tissue, or organism.

DETAILED DESCRIPTION

This invention relates to a biomaterial having a multi-dimensional structure comprising adipose tissue-derived stem cells (ASCs), an extracellular matrix, and gelatin.

As used herein, the term "biomaterial having a multi-dimensional structure" may be replaced throughout the present invention by the term "multi-dimensional biomaterial".

In one embodiment, cells are isolated from adipose tissue, and are hereinafter referred to as adipose-derived stem cells (ASCs).

In one embodiment, ASCs tissue is of animal origin, preferably of mammal origin, more preferably of human origin. Accordingly, in one embodiment, ASCs are animal ASCs, preferably mammal ASCs, more preferably human ASCs. In a preferred embodiment, ASCs are human ASCs.

Methods of isolating stem cells from adipose tissue are known in the art, and are disclosed for example in Zuk et al. (Tissue Engineering. 2001, 7:211-228). In one embodiment, ASCs are isolated from adipose tissue by liposuction.

As an illustration, adipose tissue may be collected by needle biopsy or liposuction aspiration. ASCs may be isolated from adipose tissue by first washing the tissue sample extensively with phosphate-buffered saline (PBS), optionally containing antibiotics, for example 1% Penicillin/Streptomycin (P/S). Then the sample may be placed in a sterile tissue culture plate with collagenase for tissue digestion (for example, Collagenase Type I prepared in PBS containing 2% P/S), and incubated for 30 min at 37° C., 5% CO2. The collagenase activity may be neutralized by adding culture medium (for example DMEM containing 10% serum). Upon disintegration, the sample may be transferred to a tube. The stromal vascular fraction (SVF), containing the ASCs, is obtained by centrifuging the sample (for example at 2000 rpm for 5 min). To complete the separation of the stromal cells from the primary adipocytes, the sample may be shaken vigorously to thoroughly disrupt the pellet and to mix the cells. The centrifugation step may be repeated. After spinning and the collagenase solution aspirate, the pellet may be resuspended in lysis buffer, incubated on ice (for example for 10 min), washed (for example with PBS/2% P/S) and centrifuged (for example at 2000 rpm for 5 min). The supernatant may be then aspirated, the cell pellet resuspended in medium (for example, stromal medium, i.e. α-MEM, supplemented with 20% FBS, 1% L-glutamine, and 1% P/S), and the cell suspension filtered (for example, through 70 μm cell strainer). The sample containing the cells may be finally plated in culture plates and incubated at 37° C., 5% CO2.

In one embodiment, ASCs of the invention are isolated from the stromal vascular fraction of adipose tissue. In one embodiment, the lipoaspirate may be kept several hours at room temperature, or at +4° C. for 24 hours prior to use, or below 0° C., for example −18° C., for long-term conservation.

In one embodiment, ASCs may be fresh ASCs or refrigerated ASCs. Fresh ASCs are isolated ASCs which have not undergone a refrigerating treatment. Refrigerated ASCs are isolated ASCs which have undergone a refrigerating treatment. In one embodiment, a refrigerating treatment means any treatment below 0° C. In one embodiment, the refrigerating treatment may be performed at −18° C., at −80° C. or at −180° C. In a specific embodiment, the refrigerating treatment may be cryopreservation.

As an illustration of refrigerating treatment, ASCs may be harvested at about 80-90% confluence. After steps of washing and detachment from the dish, cells may be pelleted at room temperature with a refrigerating preservation medium and placed in vials. In one embodiment, the refrigerating preservation medium comprises 80% fetal bovine serum or human serum, 10% dimethyl sulfoxide (DMSO) and 10% DMEM/Ham's F-12. Then, vials may be stored at −80° C. overnight. For example, vials may be placed in an alcohol freezing container which cools the vials slowly, at approximately 1° C. every minute, until reaching −80° C. Finally, frozen vials may be transferred to a liquid nitrogen container for long-term storage.

In one embodiment, ASCs are differentiated ASCs. In one embodiment, ASCs are differentiated into cells selected from the group comprising or consisting of osteoblasts, chondrocytes, keratinocytes, endothelial cells, myofibroblasts and adipocytes. In another embodiment, ASCs are differentiated into cells selected from the group comprising or consisting of osteoblasts, chondrocytes, keratinocytes, endothelial cells, and myofibroblasts. In another embodiment, ASCs are differentiated into cells selected from the group comprising or consisting of osteoblasts, chondrocytes, keratinocytes, and myofibroblasts. In another embodiment, ASCs are differentiated into cells selected from the group comprising or consisting of osteoblasts, chondrocytes, keratinocytes, and endothelial cells. In another embodiment, ASCs are differentiated into cells selected from the group comprising or consisting of osteoblasts, chondrocytes and keratinocytes. In another embodiment, ASCs are differentiated into cells selected from the group comprising or consisting of osteoblasts and chondrocytes.

In one embodiment, ASCs are osteogenic differentiated ACSs. In other words, in a preferred embodiment, ASCs are differentiated into osteogenic cells. In still other words, in a preferred embodiment, ASCs are differentiated in osteogenic medium. In a particular embodiment, ASCs are differentiated into osteoblasts.

Methods to control and assess the osteogenic differentiation are known in the art. For example, the osteo-differentiation of the cells or tissues of the invention may be assessed by staining of osteocalcin and/or phosphate (e.g. with von Kossa); by staining calcium phosphate (e.g. with Alizarin red); by magnetic resonance imaging (MRI); by measurement of mineralized matrix formation; or by measurement of alkaline phosphatase activity.

In one embodiment, osteogenic differentiation of ASCs is performed by culture of ASCs in osteogenic differentiation medium (MD).

In one embodiment, the osteogenic differentiation medium comprises human serum. In a particular embodiment, the osteogenic differentiation medium comprises human platelet lysate (hPL). In one embodiment, the osteogenic differentiation medium does not comprise any other animal serum, preferably it comprises no other serum than human serum.

In one embodiment, the osteogenic differentiation medium comprises or consists of proliferation medium supplemented with dexamethasone, ascorbic acid and sodium phosphate. In one embodiment, the osteogenic differentiation medium further comprises antibiotics, such as penicillin, streptomycin, gentamycin and/or amphotericin B. In one embodiment, all media are free of animal proteins.

In one embodiment, proliferation medium may be any culture medium designed to support the growth of the cells known to one of ordinary skill in the art. As used herein, the proliferation medium is also called "growth medium". Examples of growth medium include, without limitation, MEM, DMEM, IMDM, RPMI 1640, FGM or FGM-2, 199/109 medium, HamF10/HamF12 or McCoy's 5A. In a preferred embodiment, the proliferation medium is DMEM.

In one embodiment, the osteogenic differentiation medium comprises or consists of DMEM supplemented with L-alanyl-L-glutamine (Ala-Gln, also called 'Glutamax®' or 'Ultraglutamine®'), hPL, dexamethasone, ascorbic acid and sodium phosphate. In one embodiment, the osteogenic differentiation medium comprises or consists of DMEM supplemented with L-alanyl-L-glutamine, hPL, dexamethasone, ascorbic and sodium phosphate, penicillin, streptomycin and amphotericin B.

In one embodiment, the osteogenic differentiation medium comprises or consists of DMEM supplemented with L-alanyl-L-glutamine, hPL (about 5%, v/v), dexamethasone (about 1 μM), ascorbic acid (about 0.25 mM) and sodium phosphate (about 2.93 mM). In one embodiment, the osteogenic differentiation medium comprises or consists of DMEM supplemented with L-alanyl-L-glutamine, hPL (about 5%, v/v), dexamethasone (about 1 μM), ascorbic acid (about 0.25 mM) and sodium phosphate (about 2.93 mM), penicillin (about 100 U/mL) and streptomycin (about 100 μg/mL). In one embodiment, the osteogenic differentiation medium further comprises amphotericin B (about 0.1%).

In another embodiment, ASCs are chondrogenic differentiated ASCs. In other words, in a preferred embodiment, ASCs are differentiated into chondrogenic cells. In still other words, in a preferred embodiment, ASCs are differentiated in chondrogenic medium. In a particular embodiment, ASCs are differentiated into chondrocytes.

Methods to control and assess the chondrogenic differentiation are known in the art. For example, the chondrogenic differentiation of the cells or tissues of the invention may be assessed by staining of Alcian Blue.

In one embodiment, chondrogenic differentiation is performed by culture of ASCs in chondrogenic differentiation medium.

In one embodiment, the chondrogenic differentiation medium comprises or consists of DMEM, hPL, sodium pyruvate, ITS, proline, TGF-β1 and dexamethazone. In one embodiment, the chondrogenic differentiation medium further comprises antibiotics, such as penicillin, streptomycin, gentamycin and/or amphotericin B.

In one embodiment, the chondrogenic differentiation medium comprises or consists of DMEM, hPL (about 5%, v/v), dexamethasone (about 1 μM), sodium pyruvate (about 100 μg/mL), ITS (about 1×), proline (about 40 μg/mL) and TGF-β1 (about 10 ng/mL).

In another embodiment, ASCs are keratinogenic differentiated ASCs. In other words, in a preferred embodiment, ASCs are differentiated into keratinogenic cells. In still other words, in a preferred embodiment, ASCs are differentiated in keratinogenic medium. In a particular embodiment, ASCs are differentiated into keratinocytes.

Methods to control and assess the keratinogenic differentiation are known in the art. For example, the keratinogenic differentiation of the cells or tissues of the invention may be assessed by staining of Pankeratin or CD34.

In one embodiment, differentiation into keratinocytes are performed by culture of ASCs in keratinogenic differentiation medium.

In one embodiment, the keratinogenic differentiation medium comprises or consists of DMEM, hPL, insulin, KGF, hEGF, hydrocortisone and CaCl2. In one embodiment, the keratinogenic differentiation medium further comprises antibiotics, such as penicillin, streptomycin, gentamycin and/or amphotericin B.

In one embodiment, the keratinogenic differentiation medium comprises or consists of DMEM, hPL (about 5%, v/v), insulin (about 5 μg/mL), KGF (about 10 ng/mL), hEGF (about 10 ng/mL), hydrocortisone (about 0.5 μg/mL) and $CaCl_2$ (about 1.5 mM).

In another embodiment, ASCs are endotheliogenic differentiated ASCs. In still other words, in a preferred embodiment, ASCs are differentiated in endotheliogenic medium. In a particular embodiment, ASCs are differentiated into endothelial cells.

Methods to control and assess the endotheliogenic differentiation are known in the art. For example, the endotheliogenic differentiation of the cells or tissues of the invention may be assessed by staining of CD34.

In one embodiment, differentiation into endothelial cells are performed by culture of ASCs in endotheliogenic differentiation medium.

In one embodiment, the endotheliogenic differentiation medium comprises or consists of EBM™-2 medium, hPL, hEGF, VEGF, R3-IGF-1, ascorbic acid, hydrocortisone and hFGFb. In one embodiment, the endotheliogenic differentiation medium further comprises antibiotics, such as penicillin, streptomycin, gentamycin and/or amphotericin B.

In one embodiment, the endotheliogenic differentiation medium comprises or consists of EBM™-2 medium, hPL (about 5%, v/v), hEGF (about 0.5 mL), VEGF (about 0.5 mL), R3-IGF-1 (about 0.5 mL), ascorbic acid (about 0.5 mL), hydrocortisone (about 0.2 mL) and hFGFb (about 2 mL), reagents of the kit Clonetics™ EGM™-2MV BulletKit™ CC-3202 (Lonza).

In another embodiment, ASCs are myofibrogenic differentiated ASCs. In other words, in a preferred embodiment, ASCs are differentiated into myofibrogenic cells. In still other words, in a preferred embodiment, ASCs are differentiated in myofibrogenic medium. In a particular embodiment, ASCs are differentiated into myofibroblasts.

Methods to control and assess the myofibrogenic differentiation are known in the art. For example, the myofibrogenic differentiation of the cells or tissues of the invention may be assessed by staining of α-SMA.

In one embodiment, differentiation into myofibrogenic cells are performed by culture of ASCs in myofibrogenic differentiation medium.

In one embodiment, the myofibrogenic differentiation medium comprises or consists of DMEM:F12, sodium pyruvate, ITS, RPMI 1640 vitamin, TGF-β1, Glutathione, MEM. In one embodiment, the myofibrogenic differentiation medium further comprises antibiotics, such as penicillin, streptomycin, gentamycin and/or amphotericin B.

In one embodiment, the myofibrogenic differentiation medium comprises or consists of DMEM:F12, sodium pyruvate (about 100 μg/mL), ITS (about 1×), RPMI 1640 vitamin (about 1×), TGF-β1 (about 1 ng/mL), Glutathione (about 1 μg/mL), MEM (about 0.1 mM).

In another embodiment, ASCs are adipogenic differentiated ASCs. In other words, in a preferred embodiment, ASCs are differentiated into adipogenic cells. In still other words, in a preferred embodiment, ASCs are differentiated in adipogenic medium. In a particular embodiment, ASCs are differentiated into adipocytes.

Methods to control and assess the adipogenic differentiation are known in the art. For example, the adipogenic differentiation of the cells or tissues of the invention may be assessed by staining by Oil-Red.

In one embodiment, differentiation into adipocytes are performed by culture of ASCs in adipogenic differentiation medium.

In one embodiment, the adipogenic differentiation medium comprises or consists of DMEM, hPL, Dexamethazone, insulin, Indomethacin and IBMX. In one embodiment, the adipogenic differentiation medium further comprises antibiotics, such as penicillin, streptomycin, gentamycin and/or amphotericin B.

In one embodiment, the adipogenic differentiation medium comprises or consists of DMEM, hPL (about 5%), Dexamethazone (about 1 μM), insulin (about 5 μg/mL), Indomethacin (about 50 μM) and IBMX (about 0.5 mM).

In one embodiment, the ASCs are late passaged adipose-derived stem cells. As used herein, the term "late passaged" means adipose-derived stem cells differentiated at least after passage 4. As used herein, the passage 4 refers to the fourth passage, i.e. the fourth act of splitting cells by detaching them from the surface of the culture vessel before they are resuspended in fresh medium. In one embodiment, late passaged adipose-derived stem cells are differentiated after passage 4, passage 5, passage 6 or more. In a preferred embodiment, ASCs are differentiated after passage 4.

The initial passage of the primary cells was referred to as passage 0 (P0). According to the present invention, passage P0 refers to the seeding of cell suspension from the pelleted Stromal Vascular Fraction (SVF) on culture vessels. Therefore, passage P4 means that cells were detached 4 times (at P1, P2, P3 and P4) from the surface of the culture vessel (for example by digestion with trypsin) and resuspended in fresh medium.

In one embodiment, the ASCs of the invention are cultured in proliferation medium up to the fourth passage. In one embodiment, the ASCs of the invention are culture in differentiation medium after the fourth passage. Accordingly, in one embodiment, at passages P1, P2 and P3, ASCs are detached from the surface of the culture vessel and then diluted to the appropriate cell density in proliferation medium. Still according to this embodiment, at passage P4, ASCs are detached from the surface of the culture vessel and then diluted to the appropriate cell density in differentiation medium. Therefore, according to this embodiment, at P4 the ASCs of the invention are not resuspended and cultured in proliferation medium until they reach confluence before being differentiated (i.e. before being cultured in differentiation medium), but are directly resuspended and cultured in differentiation medium.

In one embodiment, cells are maintained in differentiation medium at least until they reach confluence, preferably between 70% and 100% confluence, more preferably between 80% and 95% confluence. In one embodiment, cells are maintained in differentiation medium for at least 5 days, preferably at least 10 days, more preferably at least 15 days. In one embodiment, cells are maintained in differentiation medium from 5 to 30 days, preferably from 10 to 25 days, more preferably from 15 to 20 days. In one embodiment, differentiation medium is replaced every 2 days. However, as it is known in the art, the cell growth rate from one donor to another could slightly differ. Thus, the duration of the differentiation and the number of medium changes may vary from one donor to another.

In one embodiment, cells are maintained in differentiation medium at least until formation of distinctive tissue depending on the differentiation medium used.

For example, cells may be maintained in osteogenic differentiation medium at least until formation of osteoid, i.e. the unmineralized, organic portion of the bone matrix that forms prior to the maturation of bone tissue.

Culture parameters such as, e.g., temperature, pH, $O_2$ content, $CO_2$ content and salinity may be adjusted accordingly to the standard protocols available in the state of the art.

In one embodiment, the gelatin of the invention is porcine gelatin. As used herein, the term "porcine gelatin" may be replaced by "pork gelatin" or "pig gelatin". In one embodiment, the gelatin is porcine skin gelatin.

In one embodiment, the gelatin of the invention is in form of particles, beads, spheres, microspheres, and the like.

In one embodiment, the gelatin of the invention is not structured to form a predefined 3D shape or scaffold, such as for example a cube. In one embodiment, the gelatin of the invention has not a predefined shape or scaffold. In one embodiment, the gelatin of the invention has not the form of a cube. In one embodiment, the gelatin, preferably the porcine gelatin, is not a 3D scaffold. In one embodiment, the biomaterial of the invention is scaffold-free.

In one embodiment, the gelatin of the invention is a macroporous microcarrier.

Examples of porcine gelatin particles include, but are not limited to, Cultispher® G, Cultispher® S, Spongostan and Cutanplast. In one embodiment, the gelatin of the invention is Cultispher® G or Cultispher® S.

In one embodiment, the gelatin, preferably the porcine gelatin, of the invention have a mean diameter of at least about 50 μm, preferably of at least about 75 μm, more preferably of at least about 100 μm, more preferably of at least about 130 μm. In one embodiment, the gelatin of the invention, preferably the porcine gelatin, have a mean diameter of at most about 1000 μm, preferably of at most about 750 μm, more preferably of at most about 500 μm. In another embodiment, the gelatin of the invention, preferably the porcine gelatin, have a mean diameter of at most about 450 μm, preferably of at most about 400 μm, more preferably of at least most about 380 μm.

In one embodiment, the gelatin of the invention, preferably the porcine gelatin, has a mean diameter ranging from about 50 μm to about 1000 μm, preferably from about 75 μm to about 750 μm, more preferably from about 100 μm to about 500 μm. In another embodiment, the gelatin of the invention, preferably the porcine gelatin, has a mean diameter ranging from about 50 μm to about 500 μm, preferably from about 75 μm to about 450 μm, more preferably from about 100 μm to about 400 μm. In another embodiment, the gelatin of the invention, preferably the porcine gelatin, have a mean diameter ranging from about 130 μm to about 380 μm.

Methods to assess the mean diameter of gelatin particles according to the invention are known in the art. Examples of such methods include, but are not limited to, granulometry, in particular using suitable sieves; sedimentometry; centrifugation techniques; laser diffraction; and images analysis, in particular by the means of a high-performance camera with telecentric lenses; and the like. In one embodiment, gelatin is added at a concentration ranging from about 0.1 $cm^3$ to about 5 $cm^3$ for a 150 $cm^2$ vessel, preferably from about 0.5 $cm^3$ to about 4 $cm^3$, more preferably from about 0.75 $cm^3$ to about 3 $cm^3$. In one embodiment, gelatin is added at a concentration ranging from about 1 $cm^3$ to about 2 $cm^3$ for a 150 $cm^2$ vessel. In one embodiment, gelatin is added at a concentration of about 1 $cm^3$, 1.5 $cm^3$ or 2 $cm^3$ for a 150 $cm^2$ vessel.

In one embodiment, gelatin is added at a concentration ranging from about 0.1 g to about 5 g for a 150 $cm^2$ vessel, preferably from about 0.5 g to about 4 g, more preferably from about 0.75 g to about 3 g. In one embodiment, gelatin is added at a concentration ranging from about 1 g to about 2 g for a 150 $cm^2$ vessel. In one embodiment, gelatin is added at a concentration of about 1 g, 1.5 g or 2 g for a 150 $cm^2$ vessel.

In one embodiment, the gelatin of the invention is added to the culture medium after differentiation of the cells. In one embodiment, the gelatin of the invention is added to the culture medium when cells are sub-confluent. In one embodiment, the gelatin of the invention is added to the culture medium when cells are overconfluent. In one embodiment, the gelatin of the invention is added to the culture medium when cells have reached confluence after differentiation. In others words, in one embodiment, the gelatin of the invention is added to the culture medium when cells have reached confluence in differentiation medium. In one embodiment, the gelatin of the invention is added to the culture medium at least 5 days after P4, preferably 10 days, more preferably 15 days. In one embodiment, the gelatin of the invention is added to the culture medium from 5 to 30 days after P4, preferably from 10 to 25 days, more preferably from 15 to 20 days.

In one embodiment, the biomaterial according to the invention is two-dimensional. In this embodiment, the biomaterial of the invention may form a thin film of less than 1 mm.

Within the scope of the invention, the expression "less than 1 mm" encompasses 0.99 mm, 0.95 mm, 0.9 mm, 0.8 mm, 0.75 mm, 0.7 mm, 0.6 mm, 0.5 mm, 0.4 mm, 0.3 mm, 0.2 mm, 0.1 mm and less. In some embodiments, the expression "less than" may be substituted with the expression "inferior to".

In another embodiment, the biomaterial according to the invention is three-dimensional. In this embodiment, the biomaterial of the invention may form a thick film having a thickness of at least 1 mm. The size of the biomaterial may be adapted to the use.

Within the scope of the invention, the expression "at least 1 mm" encompasses 1 mm, 1.2 mm, 1.3 mm, 1.5 mm, 1.6 mm, 1.75 mm, 1.8 mm, 1.9 mm, 2 mm, 2.25 mm, 2.5 mm, 2.75 mm, 3 mm, 3.5 mm, 4 mm, 4.5 mm, 5 mm and more. In some embodiments, the expression "at least 1 mm" may be substituted with the expression "equal or superior to 1 mm".

In one embodiment, the biomaterial of the invention does not comprise a scaffold. As used herein, the term "scaffold" means a structure that mimics the porosity, pore size, and/or function of native mammal tissues, including human and animal tissues, such as native mammal bones or scaffold mimicking natural extracellular matrix structure. Examples of such scaffolds include, but are not limited to, artificial bone, collagen sponges, hydrogels, such as protein hydrogels, peptide hydrogels, polymer hydrogels and wood-based nanocellulose hydrogels, and the like. In one embodiment, the biomaterial of the invention does not comprise an artificial bone. In one embodiment, the biocompatible material of the invention is not an artificial bone. In one embodiment, the biomaterial of the invention does not comprise an artificial dermis and/or epidermis. In one embodiment, the biocompatible material of the invention is not an artificial dermis and/or epidermis.

In one embodiment, the multi-dimension of the biomaterial of the invention is not due to a scaffold mimicking natural extracellular matrix structure. In one embodiment, the biomaterial of the invention does not comprise a scaffold mimicking natural extracellular matrix structure.

In one embodiment, the multi-dimension of the biomaterial of the invention is due to the synthesis of extracellular matrix by adipose tissue-derived stem cells of the invention.

In one embodiment, the biomaterial of the invention comprises an extracellular matrix. In one embodiment, the extracellular matrix of the biomaterial of the invention derived from the ASCs.

As used herein, the term "extracellular matrix" means a non-cellular three-dimensional macromolecular network. Matrix components of ECM bind each other as well as cell adhesion receptors, thereby forming a complex network into which cells reside in tissues or in biomaterials of the invention.

In one embodiment, the extracellular matrix of the invention comprises collagen, proteoglycans/glycosaminoglycans, elastin, fibronectin, laminin, and/or other glycoproteins. In a particular embodiment, the extracellular matrix of the invention comprises collagen. In another particular embodiment, the extracellular matrix of the invention comprises proteoglycans. In another particular embodiment, the extracellular matrix of the invention comprises collagen and proteoglycans. In one embodiment, the extracellular matrix of the invention comprises growth factors, proteoglycans, secreting factors, extra-cellular matrix regulators, and glycoproteins.

In one embodiment, the ASCs within the biomaterial of the invention form a tissue, herein referred to as ASCs tissue.

In one embodiment, the ASCs tissue is a cellularized interconnective tissue. In one embodiment, the biocompatible material, preferably the biocompatible particles, is integrated in the cellularized interconnective tissue. In one embodiment, the biocompatible material, preferably the biocompatible particles, is dispersed within the ASCs tissue.

In one embodiment, the biomaterial of the invention is characterized by an interconnective tissue formed through gelatin. In one embodiment, the biomaterial of the invention is characterized by mineralization surrounding gelatin.

In one embodiment, when osteogenic differentiation medium is used, the biomaterial of the invention has the same properties as a real bone with osteocalcin expression and mineralization properties. According to this embodiment, the biomaterial of the invention comprises osseous cells. Still according to this embodiment, the biomaterial of the invention comprises osseous cells and an extracellular matrix. Still according to this embodiment, the biomaterial of the invention comprises osseous cells and collagen. Still according to this embodiment, the biomaterial of the invention comprises an osseous matrix.

In one embodiment, the biomaterial of the invention is such that the differentiation of the cells of the biomaterial has reached an end point, and the phenotype of the biomaterial will remain unchanged when implanted.

In one embodiment, the biomaterial of the invention comprises growth factors. In one embodiment, the biomaterial of the invention comprises VEGF and/or SDF-1$\alpha$.

In one embodiment, the biomaterial according to the invention is mineralized. As used herein, the term "mineralization" or "bone tissue mineral density" refers to the amount of mineral matter per square centimeter of bones or "bone-like" tissues formed by biomaterial, also expressed in percentage. Accordingly, as used herein, the term "mineralization" or "bone tissue mineral density" refers to the amount of mineral matter per square centimeter of biomaterial, also expressed in percentage.

Methods to assess the mineralization degree of a biomaterial are known in the art. Examples of such methods include, but are not limited to, micro-computed tomography (micro-CT) analysis, imaging mass spectrometry, calcein blue staining, Bone Mineral Density Distribution (BMDD) analysis, and the like.

In one embodiment, the mineralization of the biomaterial of the invention increases with maturation of the biomaterial. As used herein, the term "maturation of the biomaterial" means the duration of the culture with gelatin. In other words, the maturation of the biomaterial corresponds to the time of multi-dimensional induction.

In one embodiment, the mineralization degree of the biomaterial of the invention is less than 1%. In one embodiment, mineralization degree less than 1% is obtained with a maturation inferior to 12 weeks into osteogenic differentiation medium. In one embodiment, mineralization degree less than 1% is obtained with a maturation inferior or equal to 8 weeks into osteogenic differentiation medium.

In one embodiment, the mineralization degree of the biomaterial of the invention ranges from about 1% to about 20%, preferably from about 1% to about 15%, more preferably from about 1% to about 10%, even more preferably from about 1% to about 5%. In one embodiment, the mineralization degree of the biomaterial of the invention ranges from about 1% to about 4% or 3%. Within the scope of the invention, the expression "about 1% to about 20%" encompasses about 1%, 2%, 3%, 4%, 5%, 6%, 7%, 8%, 9%, 10%, 11%, 12%, 13%, 14%, 15%, 16%, 17%, 18%, 19% and about 20%.

In another embodiment, the mineralization degree of the biomaterial of the invention is of at least 1% or 1.24%. In one embodiment, mineralization degree of at least 1% or 1.24% is obtained with a maturation superior or equal to 12 weeks into osteogenic differentiation medium.

In another embodiment, the mineralization degree of the biomaterial of the invention is of at least 2%, 2.5% or 2.77%. In one embodiment, mineralization degree of at least 2%, 2.5% or 2.77% is obtained with a maturation superior or equal to 25 weeks into osteogenic differentiation medium.

In one particular embodiment, the mineralization degree of the biomaterial of the invention is of about 0.07%. In another particular embodiment, the mineralization degree of the biomaterial of the invention is of about 0.28%. In another particular embodiment, the mineralization degree of the biomaterial of the invention is of about 0.33%. In another particular embodiment, the mineralization degree of the biomaterial of the invention is of about 1.24%. In another particular embodiment, the mineralization degree of the biomaterial of the invention is of about 2.77%.

This present invention also relates to a method for producing a multi-dimensional structure comprising differentiated adipose-derived stem cells (ASCs), an extracellular matrix and gelatin.

In one embodiment, the method for producing the biomaterial according to the invention comprises the steps of:

cell proliferation, cell differentiation, and multi-dimensional induction.

In one embodiment, the method for producing the biomaterial according to the invention comprises the steps of:

ASCs proliferation,

ASCs differentiation, and 3-dimensional induction.

In one embodiment, the method for producing the biomaterial according to the invention comprises the steps of:

isolating cells, preferably ASCs, from a subject;

proliferating cells, preferably ASCs, differentiating the proliferated cells, preferably ASCs, and culturing the differentiated cells, preferably ASCs, in the presence of a gelatin.

In one embodiment, the method for producing the biomaterial of the invention further comprises a step of isolation of cells, preferably ASCs, performed before the step of cell proliferation. In one embodiment, the method for producing the biomaterial of the invention further comprises a step of isolating cells, preferably ASCs, performed before the step of cell proliferation.

In one embodiment, the step of proliferation is performed in proliferation medium. In a particular embodiment, the proliferation medium is DMEM. In one embodiment, the proliferation medium is supplemented with Ala-Gln and/or human platelet lysate (hPL). In one embodiment, the proliferation medium further comprises antibiotics, such as penicillin and/or streptomycin.

In one embodiment, the proliferation medium comprises or consists of DMEM supplemented with Ala-Gln and hPL (5%). In one embodiment, the proliferation medium comprises or consists of DMEM supplemented with Ala-Gln, hPL (5%, v/v), penicillin (100 U/mL) and streptomycin (100 μg/mL).

In one embodiment, the step of proliferation is performed as described herein above. In one embodiment, the step of proliferation is performed up to P8. In one embodiment, the step of proliferation lasts up to P4, P5, P6, P7 or P8. Accordingly, in one embodiment, the step of cell proliferation includes at least 3 passages. In one embodiment, the step of cell proliferation includes at most 7 passages. In one embodiment, the step of cell proliferation includes from 3 to 7 passages. In one particular embodiment, the step of proliferation is performed up to P4. Accordingly, in one embodiment, the step of cell proliferation includes detaching cells from the surface of the culture vessel and then diluting them in proliferation medium at passages P1, P2 and P3. In an embodiment of a proliferation up to P6, the step of cell proliferation includes detaching cells from the surface of the culture vessel and then diluted them in proliferation medium at passages P1, P2, P3, P4 and P5.

In one embodiment, the step of proliferation lasts as long as necessary for the cells to be passed 3, 4, 5, 6 or 7 times. In a particular embodiment, the step of proliferation lasts as long as necessary for the cells to be passed 3 times. In one embodiment, the step of proliferation lasts until cells reach confluence after the last passage, preferably between 70% and 100% confluence, more preferably between 80% and 95% confluence. In one embodiment, the step of proliferation lasts until cells reach confluence after the third, fourth, fifth, sixth or seventh passage.

In an advantageous embodiment, culturing cells, preferably ASCs, in differentiation medium before adding gelatin is a key step of the method of the invention. Such a step is necessary for allowing the differentiation of the ASCs into osteogenic cells. In addition, this step is necessary for obtaining a multi-dimensional structure.

In one embodiment, the step of differentiation is performed after P4, P5, P6, P7 or P8. In one embodiment, the step of differentiation is performed when cells are not at confluence. In a particular embodiment, the step of differentiation is performed after P4, P5, P6, P7 or P8 without culture of cells up to confluence.

In one embodiment, the step of differentiation is performed at P4, P5, P6, P7 or P8. In one embodiment, the step of differentiation is performed when cells are not at confluence. In a particular embodiment, the step of differentiation is performed at P4, P5, P6, P7 or P8 without culture of cells up to confluence.

In one embodiment, the step of differentiation is performed by incubating cells in a differentiation medium. In one embodiment, the step of differentiation is performed by incubating cells in an osteogenic, chondrogenic, myofibrogenic or keratinogenic differentiation medium, preferably in a in an osteogenic, chondrogenic or myofibrogenic differentiation medium, more preferably in an osteogenic or chondrogenic differentiation medium, more preferably an osteogenic medium. In one embodiment, the step of differentiation is performed by resuspending cells detached from the surface of the culture vessel in differentiation medium.

In one embodiment, the incubation of ASCs in differentiation medium is carried out for at least 3 days, preferably at least 5 days, more preferably at least 10 days, more preferably at least 15 days. In one embodiment, the incubation of ASCs in differentiation medium is carried out from 5 to 30 days, preferably from 10 to 25 days, more preferably from 15 to 20 days. In one embodiment, the differentiation medium is replaced every 2 days. Within the scope of the invention, the expression "at least 3 days" encompasses 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 days and more.

In one embodiment, the step of multi-dimensional induction, preferably 3D induction, is performed by adding gelatin as defined hereinabove in the differentiation medium. In one embodiment, cells are maintained in differentiation medium during the step of multi-dimensional induction, preferably 3D induction.

In one embodiment, the step of multi-dimensional induction, preferably 3D induction, is performed when cells reach confluence in the differentiation medium, preferably between 70% and 100% confluence, more preferably between 80% and 95% confluence.

In another embodiment, the step of multi-dimensional induction, preferably 3D induction, is performed when a morphologic change appears. In one embodiment, the step of multi-dimensional induction, preferably 3D induction, is performed when at least one distinctive tissue occurs, depending on the differentiation medium used. For example, when osteogenic differentiation medium is used, the step of multi-dimensional induction, preferably 3D induction, is performed when at least one osteoid nodule is formed. As used herein, the term "osteoid" means an un-mineralized, organic portion of bone matrix that forms prior to the maturation of bone tissue.

In another embodiment, the step of multi-dimensional induction, preferably 3D induction, is performed when cells reach confluence.

In one embodiment, cells and gelatin of the invention are incubated for at least 5 days, preferably at least 10 days, more preferably at least 15 days. In one embodiment, cells and gelatin of the invention are incubated from 10 days to 30 days. Within the scope of the invention, the expression "at least 5 days" encompasses 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 days and more.

In another embodiment, cells and gelatin of the invention are incubated for at least 1 week, 2 weeks, 3 weeks, 4 weeks, 8 weeks, 12 weeks, 25 weeks or 34 weeks.

In one embodiment, the medium is replaced every 2 days during the step of multi-dimensional induction, preferably 3D induction.

The invention also relates to a multi-dimensional biomaterial obtainable by the method according to the invention. In one embodiment, the multi-dimensional biomaterial is obtained by the method according to the invention. In one embodiment, the multi-dimensional biomaterial is produced by the method according to the invention. In one embodiment, the biomaterial obtainable or obtained by the method of the invention is intended to be implanted in a human or animal body. In one embodiment, the implanted biomaterial may be of autologous origin, or allogenic. In one embodiment, the biomaterial of the invention may be implanted in a bone, cartilage, dermis, muscle, endothelial or adipose tissue area. In one embodiment, this biomaterial may be implanted in irregular areas of the human or animal body.

In one embodiment, the biomaterial of the invention is homogeneous, which means that the structure and/or constitution of the biomaterial are similar throughout the whole tissue. In one embodiment, the biomaterial has desirable handling and mechanical characteristics required for implantation in the native disease area. In one embodiment, the biomaterial obtainable or obtained by the method of the invention can be held with a surgical instrument without being torn up.

Another object of the present invention is a medical device comprising a biomaterial according to the invention.

Still another object is a pharmaceutical composition comprising a biomaterial according to the invention and at least one pharmaceutically acceptable carrier.

The present invention also relates to a biomaterial or a pharmaceutical composition according to the invention for use as a medicament.

The invention relates to any use of the biomaterial of the invention, as a medical device or included into a medical device, or in a pharmaceutical composition. In certain embodiments, the biomaterial, medical device or pharmaceutical composition of the invention is a putty-like material that may be manipulated and molded prior to use.

The present invention further relates to a biomaterial having a multi-dimensional structure comprising differentiated adipose-derived stem cells (ASCs), an extracellular matrix and gelatin, a medical device or a pharmaceutical composition comprising the same, for use for, or for use in, treating a tissue defect in a subject in need thereof.

Another aspect of the invention also relates to the use of a biomaterial having a multi-dimensional structure comprising differentiated adipose-derived stem cells (ASCs), an extracellular matrix and gelatin, a medical device or a pharmaceutical composition comprising the same, for treating a tissue defect. A still other aspect of the invention also relates to the use of a biomaterial having a multi-dimensional structure comprising differentiated adipose-derived stem cells (ASCs), an extracellular matrix and gelatin, a medical device or a pharmaceutical composition comprising the same, for the preparation or the manufacture of a medicament for treating a tissue defect.

The present invention further relates to a method of treating tissue defect in a subject in need thereof comprising administering to the subject a therapeutically effective amount of a biomaterial, medical device or pharmaceutical composition according to the invention.

One aspect of the invention is a method of tissue reconstruction in a subject in need thereof comprising administering to the subject a therapeutically effective amount of a biomaterial, medical device or pharmaceutical composition according to the invention.

As used herein, the term "tissue reconstruction" may be replaced by "tissue repair" or "tissue regeneration".

In one embodiment, the term "tissue" comprises or consists of bone, cartilage, dermis, epidermis, muscle, endothelium, and adipose tissue. Accordingly, in one embodiment, tissue defect comprises or consists of bone, cartilage, dermis, epidermis, muscle, endothelium and adipose tissue defect.

In one embodiment, tissue reconstruction is selected from the group comprising or consisting of bone reconstruction, cartilage reconstruction, dermis reconstruction, epidermis reconstruction, muscle or myogenic reconstruction, endothelial reconstruction and adipogenic reconstruction.

Examples of bone and dermis and/or epidermis reconstruction include, but are not limited to, dermal reconstruction, wound healing, diabetic ulcer treatment such as diabetic foot ulcer, post-burn lesions reconstruction, post-radiation lesions reconstruction, reconstruction after breast cancer or breast deformities.

Examples of dermis and/or epidermis reconstruction include, but are not limited to, dermal reconstruction, wound healing, diabetic ulcer treatment such as diabetic foot ulcer, post-burn lesions reconstruction, post-radiation lesions reconstruction, reconstruction after breast cancer or breast deformities.

Examples of cartilage reconstruction include, but are not limited to, knee chondroplasty, nose or ear reconstruction, costal or sternal reconstruction.

Examples of myogenic reconstruction include, but are not limited to, skeletal muscle reconstruction, reconstruction after break of the abdominal wall, reconstruction after ischemic muscular injury of lower limbs, reconstruction associated with compartment syndrome (CS).

Examples of endothelial reconstruction include, but are not limited to, recellularization of vascular patches for vascular anastomosis such as venous arteriosclerosis shunt.

Examples of adipogenic reconstruction include, but are not limited to, esthetic surgery, rejuvenation, lipofilling reconstruction.

The Applicant demonstrated that the biomaterial of the invention has osteogenic properties with the presence of mineralized tissue in the implant site.

In one particular aspect, the invention relates to the biomaterial, medical device or pharmaceutical composition of the invention for use in treating bone defects. In one particular aspect, the invention relates to the biomaterial, medical device or pharmaceutical composition of the invention for use for bone reconstruction. In one embodiment, the biomaterial of the invention is for use for filling a bone cavity with the human or animal body.

In one embodiment, the biomaterial, medical device or pharmaceutical composition of the invention is for use in treating cartilage defects. In one embodiment, the biomaterial, medical device or pharmaceutical composition of the invention is for use for cartilage reconstruction. In one embodiment, the biomaterial, medical device or pharmaceutical composition of the invention is for use for knee chondroplasty, nose or ear reconstruction, costal or sternal reconstruction.

The Applicant demonstrated that the biomaterial of the invention has the advantages of a faster epidermal and dermal reconstruction, elicitation of an immune response and increase of the number of elastin fibers. Moreover, the scar formed after implantation of the biomaterial of the invention is not hypertrophic.

In one embodiment, the biomaterial, medical device or pharmaceutical composition of the invention is for use in treating dermis and/or epidermis defects. In one embodiment, the biomaterial, medical device or pharmaceutical composition of the invention is for use for dermis reconstruction. In one embodiment, the biomaterial, medical device or pharmaceutical composition of the invention is for use for skin reconstruction. In one embodiment, the biomaterial, medical device or pharmaceutical composition of the invention is for dermal reconstruction, wound healing, diabetic ulcer treatment such as diabetic foot ulcer, post-burn lesions reconstruction, post-radiation lesions reconstruction, reconstruction after breast cancer or breast deformities. In a particular embodiment, the biomaterial, medical device or pharmaceutical composition of the invention is for use for, or for use in treating, dermis wound, preferably diabetic dermis wound.

In one embodiment, the biomaterial, medical device or pharmaceutical composition of the invention is for promoting the closure of wound. In one embodiment, the biomaterial, medical device or pharmaceutical composition of the invention is for reducing the thickness of wound, in particular during wound healing.

In a particular embodiment, the biomaterial, medical device or pharmaceutical composition of the invention is for use for, or for use in treating, epidermolysis bulbosa, giant congenital nevi, and/or aplasia cutis congenita.

In still another aspect, the invention relates to the biomaterial, medical device or pharmaceutical composition of the invention for use for reconstructive or aesthetic surgery.

In one embodiment, the biomaterial of the invention may be used as an allogeneic implant or as an autologous implant. In one embodiment, the biomaterial of the invention may be used in tissue grafting.

In one embodiment, the subject has already been treated for tissue defect. In another embodiment, the subject has not already been treated for a tissue defect.

In one embodiment, the subject was non-responsive to at least one other treatment for a tissue defect.

In one embodiment, the subject is diabetic. In one embodiment, the subject is suffering from a diabetic wound.

In one embodiment, the subject is an adult, i.e. is 18 years old or over. In another embodiment, the subject is a child, i.e. is under 18 years old.

In one embodiment, the biomaterial, medical device or pharmaceutical composition of the invention is administered to the subject in need thereof during a procedure of tissue reconstruction.

In some embodiments, the biomaterial, medical device or pharmaceutical composition of the invention is administered to the subject in need thereof by surgical implantation, for example via clips or a trocar; or by laparoscopic route.

The invention also relates to a kit, comprising a biomaterial, a pharmaceutical composition or a medical device according to the invention and suitable fixation means. Examples of suitable fixation means include, but are not limited to, surgical glue, tissue-glue, or any adhesive composition for surgical use which is biocompatible, non-toxic, and optionally bioresorbable.

BRIEF DESCRIPTION OF THE DRAWINGS

FIG. 1A: biomaterial formed with porcine gelatin (Cultispher G) and ASCs at 2.5 weeks of culture in osteodifferentiation medium. FIG. 1B: biomaterial formed with porcine gelatin (Cultispher G) and ASCs at 7.5 weeks of culture in osteodifferentiation medium.

FIGS. 2A-2B are photographs showing hematoxylin-eosin stainings of a biomaterial formed with porcine gelatin (Cultispher G) and ASCs at 7.5 weeks of culture in osteodifferentiation medium. FIG. 2A: Original magnification ×5. FIG. 2B: enlargement ×10.

FIGS. 3A-3B are photographs showing Von Kossa stainings of a biomaterial formed with porcine gelatin (Cultispher G) and ASCs at 7.5 weeks of culture in osteodifferentiation medium. FIG. 3A: Original magnification. FIG. 3B: enlargement ×10.

FIGS. 4A-4B are photographs showing osteocalcin expression of a biomaterial formed with porcine gelatin (Cultispher G) and ASCs at 7.5 weeks of culture in osteodifferentiation medium. FIG. 4A: Original magnification. FIG. 4B: enlargement ×10.

FIGS. 5A-5L are graphs showing expression of genes in the biomaterial of the invention formed with ASCs and Cultipher G (biomaterial) in osteodifferentiation medium compared to ASCs in MP (MP). FIG. 5A: ANG; FIG. 5B: ANGPT1; FIG. 5C: EPHB4; FIG. 5D: EDN1; FIG. 5E: THBS1; FIG. 5F: PTGS1; FIG. 5G: LEP; FIG. 5H: VEGFA; FIG. 5I: VEGFB; FIG. 5J: VEGFC; FIG. 5K: ID1; and FIG. 5L: TIMP1. *: $p<0.05$.

FIGS. 6A-6D are photographs showing the biomaterial of the invention formed with ASCs and Cultipher G at different maturation levels in osteodifferentiation medium. FIG. 6A: 4 weeks; FIG. 6B: 8 weeks; FIG. 6C: 12 weeks; and FIG. 6D: 25 weeks. Mineralization are displayed in yellow in the 3D matrix shown in transparent.

FIG. 12A: at day 29 post-implantation of a biomaterial formed with porcine gelatin (Cultispher G or S) and ASCs at 7.5 weeks of culture in osteodifferentiation medium. FIG. 12B: at day 29 post-implantation of a biomaterial formed with porcine gelatin (Cultispher G or S) alone.

FIG. 13A: without implantation; FIG. 13B: after implantation of Cultispher S particles alone; and FIG. 13C: after implantation of a biomaterial formed with porcine gelatin (Cultispher S) and ASCs at 8 weeks of culture in osteodifferentiation medium (C). Left limbs: ischemic legs; right limbs: non-ischemic legs.

FIG. 15A: on non-ischemic legs; FIG. 15B: on ischemic legs.

FIG. 16A: non-ischemic legs; FIG. 16B: ischemic legs.

FIG. 17A: no treatment (sham control). FIG. 17B: with Cultispher S particles alone. FIG. 17C: with a biomaterial formed with porcine gelatin (Cultispher S) and ASCs at 8 weeks of culture in osteodifferentiation medium.

FIG. 18A: in an ischaemic model. FIG. 18B: in a non-ischaemic model.

FIGS. 19A-19D are histograms showing epidermal and dermal scores on non-ischemic legs at day 1, 5, 15 and 34 after treatment with Cultispher S particles alone (dotted histograms) or a biomaterial formed with porcine gelatin (Cultispher S) and ASCs at 8 weeks of culture in osteodifferentiation medium (black histograms), or not treated (sham, striped histograms). FIG. 19A: epidermal score of the core of non-ischemic leg. FIG. 19B: epidermal score of the periphery of non-ischemic leg. FIG. 19C: dermal score of the core of non-ischemic leg. FIG. 19D: dermal score of the periphery of non-ischemic leg.

FIGS. 20A-20D are photographs showing structures obtained with ASCs and particles in different medium. FIG. 20A: osteogenic medium; FIG. 20B: chondrogenic medium; FIG. 20C: myofibrogenic medium; and FIG. 20D: keratinogenic medium. Form of the structure (1.), grippability (2.), hematoxylin-eosin staining (3.) and tissue-specific stainings (4.), namely osteocalcin (OC) for osteogenic medium, alcian blue (AB) for chondrogenic medium, α-SMA for myofibrogenic medium, and CD34 for keratinogenic medium, were assessed.

EXAMPLES

Figure 1A:
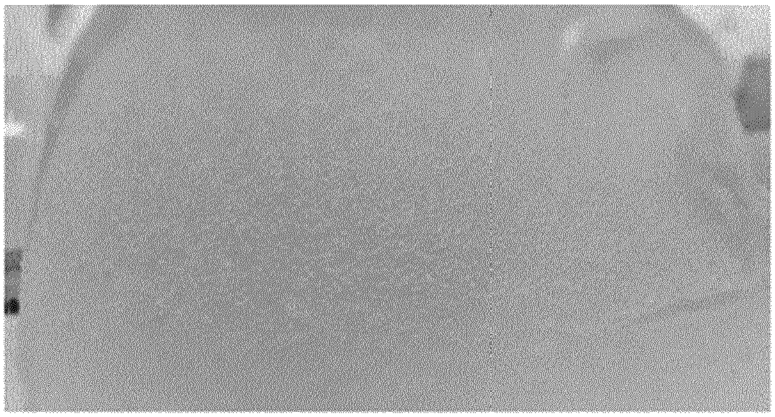
FIGS. 1A-1B are photographs showing macroscopic views of a biomaterial.

The present invention is further illustrated by the following examples.

Example 1: Production of Biomaterials of the Invention 1.1. Isolation of hASCs Human subcutaneous adipose tissues were harvested by lipo-aspiration following Coleman technique in the abdominal region and after informed consent and serologic screening.

Human adipose-derived stem cells (hASCs) were promptly isolated from the incoming adipose tissue. Lipoaspirate can be stored at +4° C. for 24 hours or for a longer time at −80° C.

First, a fraction of the lipoaspirate was isolated for quality control purposes and the remaining volume of the lipoaspirate was measured. Then, the lipoaspirate was digested by a collagenase solution (NB 1, Serva Electrophoresis GmbH, Heidelberg, Germany) prepared in HBSS (with a final concentration of ~8 U/mL). The volume of the enzyme solution used for the digestion was the double of the volume of the adipose tissue. The digestion was performed during 50-70 min at 37° C.±1° C. A first intermittent shaking was performed after 15-25 min and a second one after 35-45 min. The digestion was stopped by the addition of MP medium (proliferation medium, or growth medium). The MP medium comprised DMEM medium (4.5 g/L glucose and 4 mM Ala-Gln; Sartorius Stedim Biotech, Gottingen, Germany) supplemented with 5% human platelet lysate (hPL) (v/v). DMEM is a standard culture medium containing salts, amino acids, vitamins, pyruvate and glucose, buffered with a carbonate buffer and has a physiological pH (7.2-7.4). The DMEM used contained Ala-Gln. Human platelet lysate (hPL) is a rich source of growth factor used to stimulate in vitro growth of mesenchymal stem cells (such as hASCs).

The digested adipose tissue was centrifuged (500 g, 10 min, room temperature) and the supernatant was removed. The pelleted Stromal Vascular Fraction (SVF) was re-suspended into MP medium and passed through a 200-500 μm mesh filter. The filtered cell suspension was centrifuged a second time (500 g, 10 min, 20° C.). The pellet containing the hASCs was re-suspended into MP medium. A small fraction of the cell suspension can be kept for cells counting and the entire remaining cell suspension was used to seed one 75 $cm^2$ T-flask (referred as Passage P0). Cells counting was performed (for information only) in order to estimate the number of seeded cells.

The day after the isolation step (day 1), the growth medium was removed from the 75 $cm^2$ T-flask. Cells were rinsed three times with phosphate buffer and freshly prepared MP medium was then added to the flask.

1.2. Growth and Expansion of Human Adipose-Derived Stem Cells

During the proliferation phase, hASCs were passaged 4 times (P1, P2, P3 and P4) in order to obtain a sufficient amount of cells for the subsequent steps of the process.

Between P0 and the fourth passage (P4), cells were cultivated on T-flasks and fed with fresh MP medium. Cells were passaged when reaching a confluence ≥70% and ≤100% (target confluence: 80-90%). All the cell culture recipients from 1 batch were passaged at the same time. At each passage, cells were detached from their culture vessel with TrypLE (Select 1×; 9 mL for 75 $cm^2$ flasks or 12 mL for 150 $cm^2$ flasks), a recombinant animal-free cell-dissociation enzyme. TrypLe digestion was performed for 5-15 min at 37° C.±2° C. and stopped by the addition of MP medium.

Cells were then centrifuged (500 g, 5 min, room temperature), and re-suspended in MP medium. Harvested cells were pooled in order to guaranty a homogenous cell suspension. After resuspension, cells were counted.

At passages P1, P2 and P3, the remaining cell suspension was then diluted to the appropriate cell density in MP medium and seeded on larger tissue culture surfaces. At these steps, 75 $cm^2$ flasks were seeded with a cell suspension volume of 15 mL, while 150 $cm^2$ flasks were seeded with a cell suspension volume of 30 mL. At each passage, cells were seeded between $0.5\times10^4$ and $0.8\times10^4$ cells/$cm^2$. Between the different passages, culture medium was exchanged every 3-4 days. The cell behavior and growth rate from one donor to another could slightly differ. Hence the duration between two passages and the number of medium exchanges between passages may vary from one donor to another.

1.3. Osteogenic Differentiation

At passage P4 (i.e. the fourth passage), cells were centrifuged a second time, and re-suspended in MD medium (differentiation medium). After resuspension, cells were counted a second time before being diluted to the appropriate cell density in MD medium, and a cell suspension volume of 70 mL was seeded on 150 $cm^2$ flasks and fed with osteogenic MD medium. According to this method, cells were directly cultured in osteogenic MD medium after the fourth passage. Therefore, osteogenic MD medium was added while cells have not reached confluence.

The osteogenic MD medium was composed of proliferation medium (DMEM, Ala-Gln, hPL 5%) supplemented with dexamethasone (1 μM), ascorbic acid (0.25 mM) and sodium phosphate (2.93 mM).

The cell behavior and growth rate from one donor to another could slightly differ. Hence the duration of the osteogenic differentiation step and the number of medium exchanges between passages may vary from one donor to another.

1.4. Multi-Dimensional Induction of Cells

The 3D induction was launched when cells reach a confluence and if a morphologic change appears and if at least one osteoid nodule (un-mineralized, organic portion of the bone matrix that forms prior to the maturation of bone tissue) was observed in the flasks.

After being exposed to the osteogenic MD medium, the culture vessels containing the confluent monolayer of adherent osteogenic cells were slowly and homogeneously sprinkled with gelatin particles (Cultispher-G and Cultispher-S, Percell Biolytica, Astorp, Sweden) at a concentration of 1, 1.5 and 2 $cm^3$ for a 150 $cm^2$ vessel.

Cells were maintained in MD medium. Regular medium exchanges were performed every 3 to 4 days during the multi-dimensional induction. Those medium exchanges were performed by carefully preventing removal of gelatin particles and developing structure(s).

Example 2: Characterization of the Biomaterials 2.1. Materials and Methods 2.1.1. Structure/Histology The formation of a 3D structure obtained from ASCs and Cultispher G and S particles was tested. Particles of Cultispher were added on confluent ASCs at passage 4 from 6 different donors. Different volumes were tested: 1, 1.5, 2 $cm^3$ particles per vessel of 150 $cm^2$. The cells were maintained in differentiation medium (DMEM 4.5 g/L glucose with Ultraglutamine+1% penicillin/streptomycin+0.5% Amphotericin AB+dexamethasone (1 μM), ascorbic acid (0.25 mM) and sodium phosphate (2.93 mM)) with medium change every 3-4 days.

For the comparison of culture in MP and MD, biopsies of 3D structures in MD were taken at 5 days, 14 days and 8 weeks after addition of particles.

For the evaluation of the cellularity, biopsies of 3D structures were taken at 4 weeks, 8 weeks and 12 weeks after the addition of Cultispher particles.

They were fixed in formol and prepared for hematoxylin-eosin, Masson's Trichrome, Osteocalcin, and Von Kossa stainings.

The osteodifferentiation and the mineralization of the tissues were assessed on osteocalcin and Von Kossa-stained slides, respectively. The structure of the tissue, cellularity and the presence of extracellular matrix were assessed after hematoxylin-eosin and Masson's Trichrome staining.

2.1.2. Biological Activity

The in vitro study of the bioactivity was assessed by (i) extraction and quantification of growth factors VEGF, IGF1, SDF-1α in the final product and (ii) the capacity of growth factors secretion/content of the biomaterial of the invention in hypoxia and hyperglycemia (conditions of diabetic wound healing for example). In addition, (iii) bioactive properties of the biomaterial of the invention were characterized in vitro at the molecular level by qRT-PCR.

Growth Factors Content

To assess the bioactivity of the tissue formed, biopsies were taken at 4 and 8 weeks post-addition of gelatin (1.5 $cm^3$) for proteins extraction and quantification. The total protein and growth factors contents were quantified by colorimetry (BCA Protein Assay Kit, ThermoFisher Scientific) and ELISA for VEGF, SDF1α, IGF1 (Human Quantikine ELISA kits, RD Systems), according to suppliers' instructions.

Culture in Hypoxia and Hyperglycemia

To assess the bioactivity of the biomaterial of the invention and the impact of oxemia and glycemia on the bioactivity of this 3D structure, biopsies of the tissue formed with Cultispher G (1.5 $cm^3$) and ASCs from 3 donors at 8 weeks were rinsed twice with PBS and placed in duplicate in 6 wells-plates in 10 mL of MD at 4.5 g/L (hyperglycemic condition) or 1 g/L (normoglycemic condition) glucose without HPL. Plates were placed in hypoxia (1% O2) or normoxia (21% O2), 5% CO2, 37° C., for 72 hours. Supernatants were then harvested for total protein and growth factors quantification by colorimetry (BCA Protein Assay Kit, ThermoFisher Scientific) and ELISA (BMP2, BMP7, VEGF, SDF-1α, IGF1, FGFb (Human Quantikine ELISA kits, RD Systems), respectively. The tissues were treated for proteins extractions, purification and total protein and growth factors contents quantification.

qRT-PCR

The pro-angiogenic potential of the biomaterial of the invention was investigated by the analysis of the expression of genes involved in the vasculogenesis and angiogenesis. Genes expression by adipose stem cells in different states was analyzed: adipose stem cells in proliferation media (without phenotype orientation, MP), adipose stem cells in classical osteogenic media without particles (MD) and finally the biomaterial of the invention (adipose stem cells with 1.5 $cm^3$ of particles in view to induce the formation of the 3-dimension scaffold-free structure by the extracellular matrix).

Total RNA was extracted from ≥2000 ASCs cultured in proliferation medium (MP) (n=4 independent source of human adipose tissue) and from biopsies of ~1 $cm^2$ of the biomaterial of the invention (n=5) using the Qiazol lysis reagent (Qiagen, Hilden, Germany) and a Precellys homogenizer (Bertin instruments, Montigny-le-Bretonneux, France). RNAs were purified using Rneasy mini kit (Qiagen, Hilden, Germany) with an additional on column DNase digestion according to the manufacturer's instruction. Quality and quantity of RNA were determined using a spectrophotometer (Spectramax 190, Molecular Devices, California, USA). cDNA was synthesized from 0.5 μg of total RNA using $RT^2$ RNA first strand kit (Qiagen, Hilden, Germany) for osteogenic and angiogenic genes expression profiles though commercially available PCR arrays (Human $RT^2$ Profiler Assay—Angiogenesis). The ABI Quantstudio 5 system (Applied Biosystems) and SYBR Green ROX Mastermix (Qiagen, Hilden, Germany) were used for detection of the amplification product. Quantification was obtained according to the ΔΔCT method. The final result of each sample was normalized to the means of expression level of three Housekeeping genes (ACTB, B2M and GAPDH).

2.1.3. Impact of the Maturation of the Biomaterial on its Properties

The impact of the maturation of the biomaterial (also referred as "tissue") on its properties was assessed by the mineralization level evaluation, histological evaluation (cellularity determination) and bioactivity evaluation (extraction and quantification of growth factors VEGF, IGF1, SDF-1α). Maturation of the biomaterial means herein duration of culture of ASCs with Cultispher particles in differentiation medium.

Biopsies of 3D structures were taken at 4 weeks (one donor), 8 weeks (6 donors), 12 weeks (3 donors) and 25 weeks (1 donor) after the addition of Cultispher particles and fixed in formol for micro-CT scanner analysis. 3D structures mineralization was assessed using a peripheral quantitative CT machine (Skyscan 1172G, Bruker micro-CT NV, Kontich, Belgium).

In addition, biopsies of tissues (4 weeks (n=3), 8 weeks (n=8), 12 weeks (n=3) and 25 weeks (n=1)) were fixed in formol and prepared for hematoxylin-eosin, Masson's Trichrome, and Von Kossa stainings.

2.2. Results 2.2.1. Structure/Histology

No 3D structure was obtained when Cultispher particles were cultured with hASCs in proliferation medium. As no macroscopic 3D structure was found, no microscopic structure was formed.

Figure 1B:
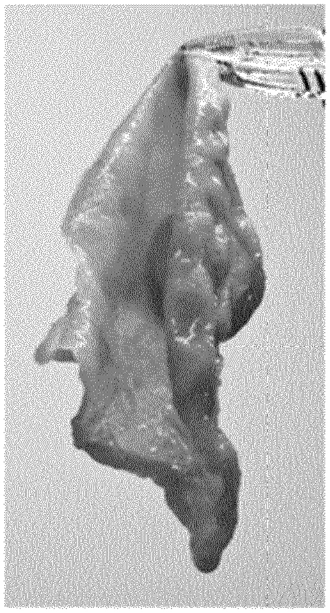

In contrast to the proliferation medium, Cultispher cultured with ASCs in osteogenic differentiation medium showed the formation of a sheet-like 3D structure (FIG. 1A). Moreover, this structure was prehensile with forceps (FIG. 1B).

Histological examination of Cultispher cultured with ASCs in osteogenic differentiation medium revealed the presence of a cellularized interconnected tissue between particles. Moreover, extracellular matrix and cells were found in the pores of particles (FIGS. 2A and B). Von Kossa staining showed the presence of isolated mineralized particles. In contrast, the extracellular matrix was not stained by Von Kossa (FIGS. 3A and B). Finally, osteocalcine expression was found in the interconnective tissue (FIGS. 4A and B).

2.2.2. Biological Activity

Growth Factors Content and Secretion

No protein content was found in Cultispher G and S alone. Only traces of IGF-1 were detected but below the lower limit of quantification of the ELISA method.

The levels IGF-1 and BMP7 detected in the supernatants of biopsies of Cultispher cultured with ASCs in osteogenic differentiation medium were below the lower limit of quantification of the ELISA methods while traces of BMP2 and FGFb were measured. In contrast, a significant secretion of VEGF and SDF-1α was found.

No significant impact of the culture conditions on the growth factors secretion were found (Table 1).

TABLE 1

Impact of culture conditions on VEGF and SDF-1α secretion by the biomaterial of the invention

| | | Secretion (ng/g) | |
|---|---|---|---|
| Oxemia | Glycemia | VEGF | SDF-1α |
| 21% O2 | 1 g/L | 74 ± 24 | 19 ± 20 |
| | 4.5 g/L | 50 ± 28 | 27 ± 27 |
| 1% O2 | 1 g/L | 130 ± 51 | 14 ± 10 |
| | 4.5 g/L | 106 ± 60 | 26 ± 10 |

The levels BMP2, BMP7 and FGFb detected in the protein extracts from the biopsies of Cultispher cultured with ASCs in osteogenic differentiation medium were below the lower limit of quantification of the ELISA methods. In contrast, a significant content in IGF-1, VEGF and SDF-1α was found.

No significant impact of the culture conditions on the VEGF content was found. However, a lower IGF-1 content in normoxia (21% O2) at 4.5 g/L glucose was found in comparison with other groups ($p<0.05$). A higher SDF-1α content was found in normoxia and normoglycemia vs hypoxia (1 and 4.5 g/L glucose) ($p<0.05$) (Table 2).

TABLE 2

Impact of culture conditions on VEGF, SDF-1α and IGF1 content of the biomaterial of the invention

| | | Secretion (ng/g) | | |
|---|---|---|---|---|
| Oxemia | Glycemia | VEGF | SDF-1α | IGF1 |
| 21% O2 | 1 g/L | 123 ± 47 | 117 ± 79** | 53 ± 37 |
| | 4.5 g/L | 104 ± 61 | 139 ± 208 | 25 ± 22* |
| 1% O2 | 1 g/L | 152 ± 80 | 36 ± 29 | 109 ± 85 |
| | 4.5 g/L | 155 ± 101 | 36 ± 44 | 94 ± 78 |

*p < 0.05 in comparison to other groups
**p < 0.05 in comparison to 1% O2 (1 and 4.5 g/L)

qRT-PCR Analysis

Over the 84 pro-angiogenic genes analyzed by qRT-PCR analysis, 13 mRNA were modulated between the different culture conditions. Ten genes were upregulated in the biomaterial of the invention in comparison to ASCs in proliferation medium (ANG, ANGPT1, EPHB4, EDN1, LEP, THBS1, PTGS1, VEGFA, VEGFB and VEGFC) and two genes were found to be down-regulated in the biomaterial of the invention in comparison to ASCs in MP (ID1, TIMP1) (FIG. 5).

A significant higher expression of angiopoietin (ANG and ANGPT1) mRNA was found in the biomaterial of the invention in comparison with ASCs in MP (FIGS. 5A and B). Angiopoietin signaling promotes angiogenesis, the process by which new arteries and veins form from preexisting blood vessels (Fagiani E et al, Cancer Lett, 2013).

EPHB4 (Ephrin receptor B4), a transmembrane protein, playing essential roles in vasculogenesis, Endothelin (EDN1), a potent vasoconstrictor (Wu M H, Nature, 2013), Thrombospondin 1 (THBS1), a vasodilatator and Cyclooxigenase 1 (PTGS1/COX-1), regulating endothelial cells were significantly up-regulated in the biomaterial of the invention compared to ASCs in MP (FIGS. 5C, D, E and F, respectively).

The expression of the Leptin (LEP) mRNA (an important enhancer of angiogenesis and inducer of the expression of VEGF; Bouloumie A et al, Circ. Res. 1998; Sierra-Honigmann M R et al, Science (New York, N.Y.) 1998) was also over-expressed in the biomaterial of the invention in comparison to ASCs in MP (FIG. 5G).

Finally, the expression of the vascular endothelial growth factor A, B and C mRNA (VEGFA/B/C) were also significantly improved for ASCs in the biomaterial of the invention in comparison to ASCs in MP (FIGS. 5H, I and J, respectively). VEGF is one of the most important growth factors for the regulation of vascular development and angiogenesis. Since bone is a highly vascularized organ (with the angiogenesis as an important regulator in the osteogenesis), the VEGF also positively impacts the skeletal development and postnatal bone repair (Hu K et al, Bone 2016).

In contrast, DNA-binding protein inhibitor (ID1) and Metallopeptidase inhibitor 1 (TIMP1), associated to reduced angiogenesis in vivo (Reed M J et al, Microvasc Res 2003) were down-regulated in the biomaterial of the invention in comparison to ASCs in MP (FIGS. 5K and L, respectively).

Overall, these molecular analyses show that the pro-angiogenic potential of ASCs is up-regulated when cells are embedded in their 3D matrix in the biomaterial of the invention.

2.2.3. Impact of the Maturation of the Biomaterial on its Properties

Mineralization Level Evaluation

Photomacrographs of the 3D grafts at 4, 8, 12 and 25 weeks revealed the same macroscopic structure (FIGS. 6A and B) and were analyzed in micro-CT. Percentage of mineralization volume were determined: 0.07% at 4 weeks, 0.28%+/−0.33% at 8 weeks, 1.24%+/−0.35% at 12 weeks and 2.77% at 25 weeks (FIGS. 6C and D).

Therefore, the higher the maturation level, the higher the mineralization.

Histological Evaluation

No impact of the maturation of the tissue on the cellular content was found as similar cellularity was quantified in the different tissues analyzed (data not shown).

In contrast, the proportion of ECM in the tissue increased with the maturation level, with a significant lower proportion of ECM at 4 weeks and a higher proportion of ECM at 25 weeks (28±7 vs 33±11/34±11 vs 56±8% of ECM at 4, 8/12 and 25 weeks, respectively ($p<0.05$)) (Table 3).

TABLE 3

Histomorphological analysis of the biomaterial of the invention at different maturation times.

| | Cells/mm$^2$ | ECM (%) |
|---|---|---|
| 4 weeks | 160 ± 104 | 28 ± 7* |
| 8 weeks | 175 ± 86 | 33 ± 11 |
| 12 weeks | 177 ± 70 | 34 ± 11 |
| 25 weeks | 191 ± 77 | 56 ± 8* |

*p < 0.05 vs other groups

A higher mineralization degree was found at 12 and 25 weeks of maturation as shown by a more marked Von Kossa staining (data not shown).

Bioactivity Evaluation

The bioactivity of the biomaterial at 4, 8, 12 and 25 weeks of maturation was studied after proteins extraction, purification and growth factors (VEGF, IGF1, SDF-1α) quantification by ELISA (Table 4).

TABLE 4

| Proteins and growth factors content in tissues at 4, 8, 12 and 25 weeks of maturation | | | |
|---|---|---|---|
| | VEGF (ng/ml) | IGF (ng/ml) | SDF-1α (ng/ml) |
| 4 weeks | 117 ± 7 | 108 ± 17 | 105 ± 42 |
| 8 weeks | 102 ± 91 | 50 ± 83 | 189 ± 180 |
| 12 weeks | 181 ± 12 | 436 ± 18 | 663 ± 27 |
| 25 weeks | 128 | 94 | 424 |

Example 3: In Vivo Study of the Angiogenic and Osteogenic Properties 3.1. Materials and Methods 3.1.1. In Vivo Experiment Using Nude Rats Ten replicates of the biomaterial of the invention (ASCs cultured as described in Example 1, with 1.5 $cm^3$ of Cultispher G or S during a maturation of 7.5 weeks) were sutured on cauterized lumbar muscle of nude rats at day 0. Twenty-nine days after implantation, biomaterials were harvested to be analyzed by imagery and histology.

3.1.2. In Vivo Experiment Using Wistar Rats

Ten replicates of the biomaterial of the invention (ASCs cultured as described in Example 1, with 1.5 $cm^3$ of Cultispher G or S during a maturation of 7.5 weeks) were sutured on cauterized lumbar muscle of Wistar rats at day 0. Twenty-nine days after implantation, biomaterials were harvested to be analyzed by imagery and histology.

The general clinical state of animals was checked daily over the course of the experimental period.

Analysis of mineralization of the 30 specimens was performed using the high-resolution X-ray micro-CT system for small-animal imaging SkyScan1076. Three-dimensional reconstructions of scans and analysis of mineralized tissue were performed using CTvol and CTan softwares (Skyscan).

Histological analyses were achieved on muscle samples in order to evaluate the in vivo angiogenic and osteoinductive properties of the products (hematoxylin-eosin, Masson's Trichrome, Von Kossa (to precise the location of the mineralization in the tissue), human tissue marker Ku80 (to confirm human origin of cells in animal tissue) and CD3 (to describe the repartition of CD3+ immune cells in the tissue) stainings.

3.2. Results 3.2.1. In Vivo Experiment Using Nude Rats

During the in vivo experiments, no sign of distress or significant lesion was noticed indicating that the product did not induce adverse effect on animals.

Figure 7:
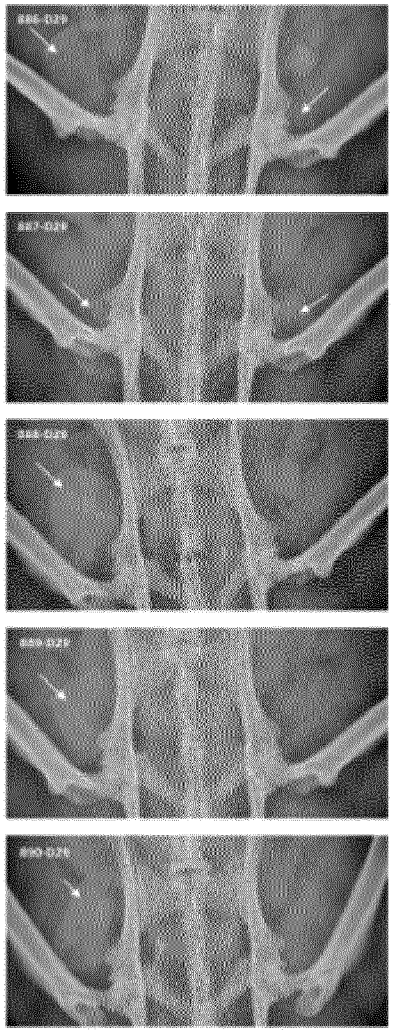
FIG. 7 is a photograph of radiographies of the "implant sites" of biomaterial formed with porcine gelatin (Cultispher G or S) and ASCs at 7.5 weeks of culture in osteodifferentiation medium in Nude rats at day 29 post-implantation.

In Nude rats, presence of radiopaque structures suggesting mineralization was observed, on the radiographs performed at day 29 (FIG. 7).

The presence of human cells was highlighted in samples from Nude rats. When present, human cells represented on average half the cells of the implant sites, edge excluded, in the two groups. Cells from rat and human origins were homogeneously distributed in the implant sites, except at the edge, where only rat cells are present.

3.2.2. In Vivo Experiment Using Wistar Rats

Figure 8:
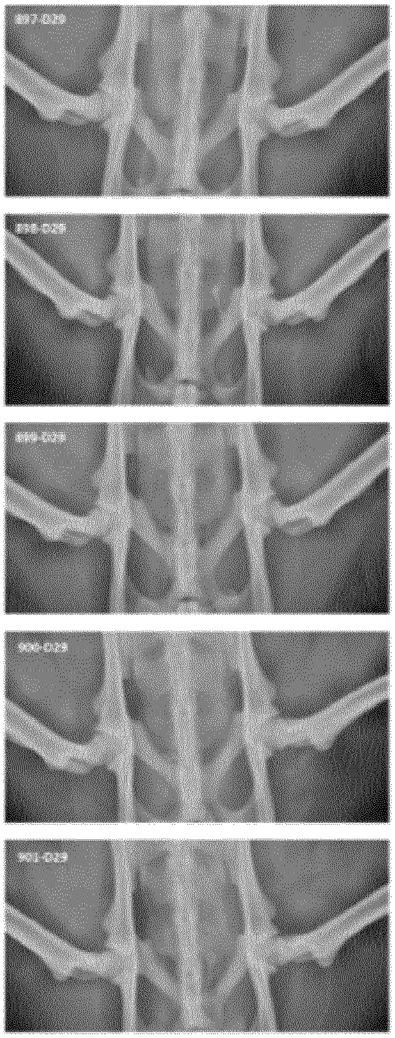
FIG. 8 is a photograph of radiographies of the "implant sites" of biomaterial formed with porcine gelatin (Cultispher G or S) and ASCs at 7.5 weeks of culture in osteodifferentiation medium in Wistar rats at day 29 post-implantation.

In Wistar rats, presence of radiopaque structures suggesting mineralization was observed, on the radiographs performed at day 29 (FIG. 8).

The analysis of the mineralization suggests the presence of mineralized tissue in each implant site.

Figure 9:
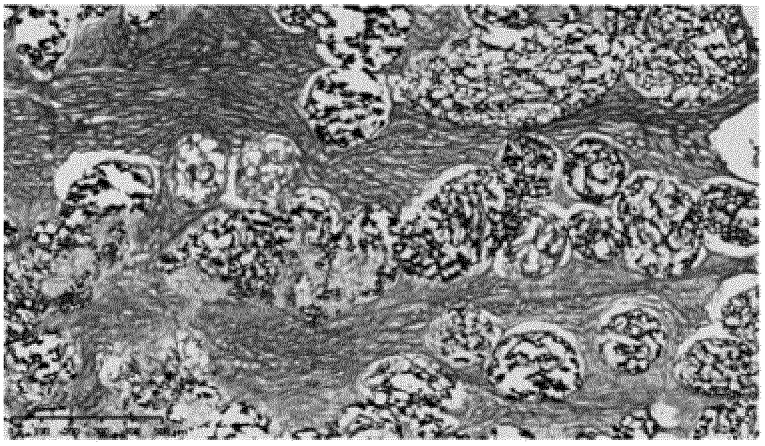
FIG. 9 is a photograph showing Von Kossa staining of a biomaterial formed with porcine gelatin (Cultispher G or S) and ASCs at 7.5 weeks of culture in osteodifferentiation medium.

Von Kossa staining indicates that the mineralization is localized on the particles (FIG. 9).

Example 4: In Vivo Bioactivity Study 4.1. Materials and Methods 4.1.1. Samples Preparation Ten Samples of ~0.5 g of biomaterial (ASCs cultured as described in Example 1, with 1.5 $cm^3$ of Cultispher S during a maturation of 8 weeks) were prepared for implantation in paravertebral musculature of 10 nude rats. In addition, 2 samples of ~0.5 g of Cultispher S particles were used as control.

In order to assess the growth factors content of the samples, a sample of biomaterial was prepared for proteins extraction and quantification (VEGF, IGF1, SDF-1α).

To evaluate the quality of the biomaterial, one sample was fixed in formol for hematoxylin-eosin (HE) and Von Kossa (VK) stainings. The assessment of the decellularization treatment efficacy was evaluated by counting the number of cells in the tissues after HE staining.

4.1.2. Housing in Animal Facilities

Animals were housed in the animal facility "Centre Préclinique Atlanthera" approved by the veterinary services and used in all the experimental procedure in agreement with the at present current legislation (Decree N 2013-118, of Feb. 1, 2013, on animals used in experimental purposes). The animals were acclimatized for a minimum of 7 days prior to the beginning of the study during whom the general state of animals was daily followed. Animals were housed in an air-conditioned animal house in plastic boxes of standard dimensions. The artificial day/night light cycle was set to 12 hours light and 12 hours darkness. All animals had free access to water and were fed ad libitum with a commercial chow. Each animal was identified by an ear tag (ring).

4.1.3. Experimental Protocol

At day 0, replicates of biomaterials were sutured on cauterized lumbar muscle of 10 nude rats while particles alone were implanted in muscular cauterized stalls realized in the lumbar muscle of 1 nude rat. Twenty-nine days after implantation, muscles containing biomaterials are harvested to be analyzed by imagery and histology.

Implantation into Lumbar Muscles

Animals were fully anaesthetized to perform the surgery under best conditions. An analgesia procedure was set up with injection of Buprenorphine almost 30 minutes before surgery followed by another injection the following day.

Surgery: for each animal, a longitudinal skin incision was made along the rachis at lumbar level. For 1 rat, muscular stalls were achieved at both sides of the skin incision (i.e. stalls were performed into the lumbar muscles). Stalls were cauterized. Particles alone were implanted into these stalls. For 10 rats, biomaterials were sutured on cauterized lumbar muscle. After the surgical procedure, the skin wounds were sutured using surgical staples.

Clinical Follow Up

The general clinical state of animals was checked daily over the course of the experimental period. Twice a week, a detailed clinical follow-up was achieved with focus on: Respiratory, eye, cardiovascular, gastrointestinal signs; Motor activity and behavior; Signs of seizure; Evaluation of the skin; Inflammation at the implantation site.

In addition, body weight was measured twice weekly at the same time of detailed clinical follow-up.

Terminal Procedures and Post-Mortem Analysis

At day 29, animals were sacrificed by exsanguination and macroscopic evaluation was achieved. During autopsy, the outside aspect of the corpse was observed and any pathological fluid loss, signing possible internal lesional anomalies, was recorded.

Thoracic and abdominal cavities were widely opened in order to evaluate any lesional modification of the intern organs, with focus on the heart, the kidneys, the spleen, the liver and the lung.

Macroscopic Evaluation at the Implant Site

Muscle implant site was exposed and a detailed macroscopic evaluation was achieved focusing on local tissue reaction and presence and localization of the implants (radiographic analysis).

Muscle implant sites were removed along. The explants were fixed in neutral-buffered formalin solution for 48 hours at room temperature.

3D Histomorphometric Analysis

Analysis of mineralization of the specimens was performed using the high-resolution X-ray micro-CT system for small-animal imaging SkyScan1076.

Muscle samples were scanned at room temperature using the following parameters: Source Voltage: 50 kV; Rotation step: 0.5°; Pixel size: 18 μm; 1 frame per position.

Three-dimensional reconstructions of scans and analysis of mineralized tissue were performed using CTvol and CTan softwares (Skyscan).

In each sample, the quantity of signal similar to those of bone mineralized tissue (threshold 40/255) was determined (identified as bone volume: BV). The "Tissue Volume" values used are the volumes of implants formulated.

Histopathologic and 2D Histomorphometric Analyses

Histological analyses were achieved on muscle samples in order to evaluate the in vivo angiogenic and osteoinductive properties of the products.

Formalin fixed explants were decalcified 13 days in EDTA 15%. Then, the samples were dehydrated and embedded in paraffin. Sections of 4-5 μm were cut using a microtome and stretched on slides. The sections were performed at two different levels distant by 150 μm.

At these two sections areas, Hematoxyline-Eosine (HE), Masson's trichrome (MT) and Immunohistochemistry of CD146 were performed (using sections from the specimens embedded in paraffin or frozen).

Images of the complete stained sections were acquired using a digital slide scanner (Nanozoomer, Hamamatsu). The quantification of area occupied by blood vessels (Trichrome Masson, CD146) was performed using NDPview2 software: A region of interest was manually delineated on the basis of the tissue features to define the area of the "implant site" on the section. Each blood vessel was delineated manually to quantify the area occupied by blood vessels in the region of interest. The surface corresponding to vessels and the number of blood vessels were reported to the total area of the "implant site".

4.2. Results 4.2.1. Histological Analyses

Figure 10:
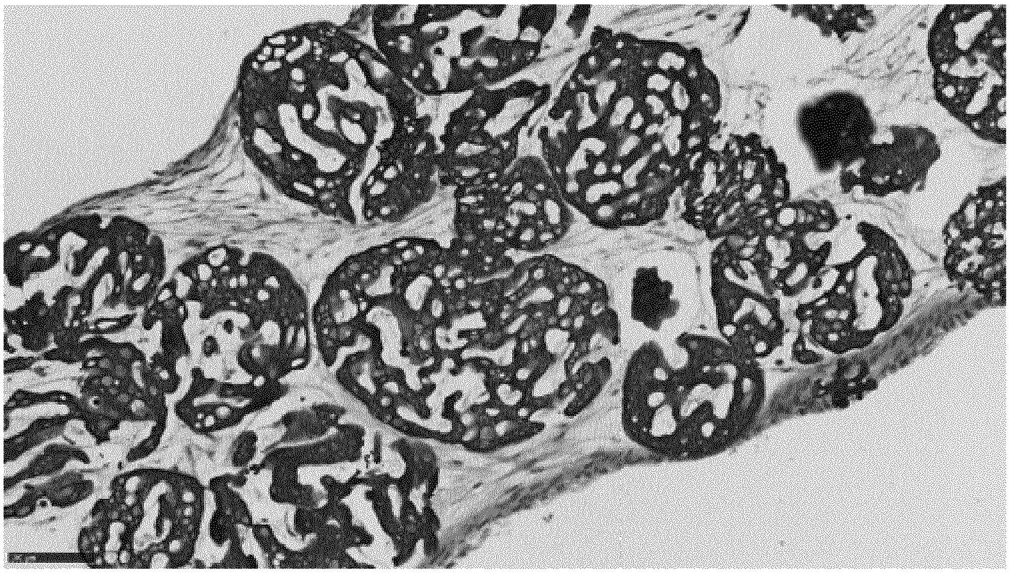
FIG. 10 is a photograph showing hematoxylin-eosin staining of a biomaterial formed with porcine gelatin (Cultispher S) and ASCs at 7.5 weeks of culture in osteodifferentiation medium.

The number of cells in the tissues was determined after HE staining (FIG. 10): 146.5±50.4 cells/mm$^2$.

Figure 11:
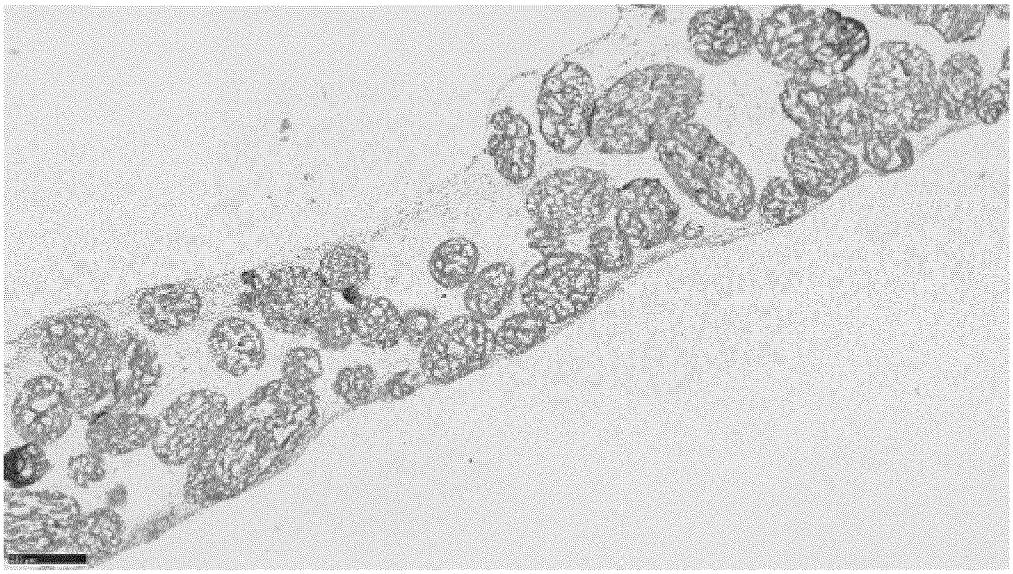
FIG. 11 is a photograph showing Von Kossa staining 29 days after implantation in a Nude rat of a biomaterial formed with porcine gelatin (Cultispher S) and ASCs at 7.5 weeks of culture in osteodifferentiation medium.

Von Kossa staining of the tissue showed a weak mineralization localized on particles (FIG. 11).

4.2.2. In Vivo Study of the Bioactivity of the Biomaterial

No sign of distress or significant lesion was noticed indicating that the product did not induce adverse effect on animal. The body weight of animals, recorded over the course of the experiment, indicated that all the animals did not present a gain of weight at day 2 and then showed a regular weight gain between day 2 and day 28. Lack of weight gain just after surgery is often observed and is not considered as a sign of any toxicity of the product tested. The regular weight gain observed between day 2 and day 28 confirms that the particles did not affect animal metabolism. At the end of in vivo experiment, the autopsy did not highlight any macroscopic organ lesion.

Mineral Content at the Implant Site

Figure 12:
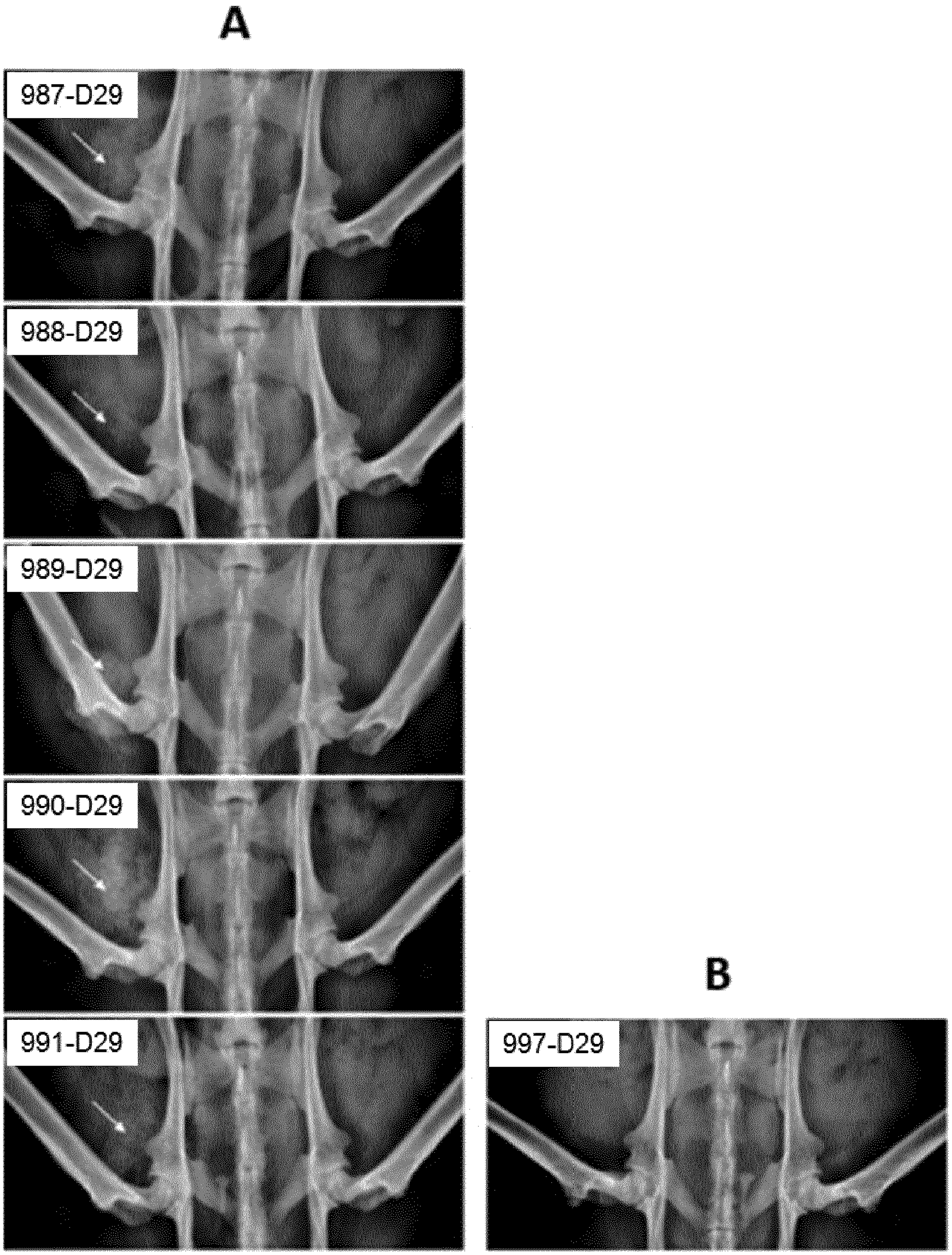
FIGS. 12A-12B are photographs showing radiographies of the "implant sites" in Nude rats.

Presence of radiopaque structures suggesting mineralization was observed, on the radiographs performed at day 29, at all the sites implanted with the biomaterial (FIG. 12).

In order to quantify the percentage of formation of mineralized tissue into the muscle, analysis of mineralization of the "implant sites" was performed using the high-resolution X-ray micro-CT system for small-animal imaging SkyScan1076. The results are presented in the Table 5.

TABLE 5

Results of high-resolution X-ray micro-CT system for small-animal imaging SkyScan1076

| Samples | BV 40/255 (mm$^3$) | TV (mm$^3$) | BV/TV (%) |
|---|---|---|---|
| NG-987 | 76.7677 | 514.6821 | 0.1492 |
| NG-988 | 22.7560 | 518.1965 | 0.0439 |
| NG-989 | 121.3495 | 470.9364 | 0.2577 |
| NG-990 | 137.0365 | 724.1618 | 0.1892 |
| NG-991 | 44.8830 | 519.4913 | 0.0864 |
| NG-992 | 23.1673 | 560.8324 | 0.0413 |
| NG-993 | 48.1291 | 496.7399 | 0.0969 |
| NG-994 | 21.2821 | 791.3064 | 0.0269 |
| NG-995 | 123.9947 | 638.3353 | 0.1942 |
| NG-996 | 52.9368 | 561.4798 | 0.0943 |

The analysis suggests the presence of a noticeable content of mineralized tissue in each site implanted with the biomaterial, with a mean of BV/TV of 0.118.

Neovascularization of the Implant

The presence of capillaries in the fibrous connective tissue was examined in order to document the neovascularization.

The number of vessels/area and the vascular density in the implants and at the junction between muscle and implant site after Masson's Trichome staining were quantified.

The implants with the biomaterial were found vascularized by Masson's Trichome staining, with a number of 40.8±18.5 vessels/mm$^2$.

Example 5: In Vivo Efficacy Study in a Hyperglycemic/Ischemic Xenogenic Rat Model 5.1. Materials and Methods 5.1.1 Animals 56 female Wistar rats of 250-300 g received streptozotocin (50 mg/kg) intraperitonaly. Seven to ten days after streptozotocin administration, blood glucose levels were measured from tail venous blood by blood glucose test strips. Rats with glucose levels >11.1 mM were considered hyperglycemic and were included in the study (n–42 rats).

Ischemia was induced in the left limb of each rat as described in Levigné et al (Biomed Res Int 2013). Through a longitudinal incision in the inguinal region that was shaved, the external iliac and femoral arteries were dissected from the common iliac to the saphenous arteries. To provoke an ischemic condition, the dissected arteries were resected from the common iliac in the left limb while in the right limb arteries were conserved and limbs considered being nonischemic. All surgical procedures were performed under an operating microscope (Carl Zeiss, Jena, Germany), and animals were anesthetized by inhalation of isoflurane 5% for induction and 3% for maintenance of anesthesia.

Animals were randomly divided into 3 groups:

Sham group (n=10 female Wistar rats);

Cultispher group (n=10 female Wistar rats), i.e. particles alone;

Biomaterial group (n=14 female Wistar rats), i.e. ASCs with gelatin particles forming a tissue.

5.1.2 Test Items 14 samples of ~0.5 g of Cultispher particles were prepared, gamma-irradiated.

14 Samples of ~2 $cm^2$ of biomaterial (ASCs cultured as described in Example 1, with 1.5 $cm^3$ of Cultispher S during a maturation of 8 weeks) were prepared for implantation.

In order to assess the growth factors content of the samples, one sample of biomaterial was prepared for proteins extraction and quantification (VEGF, IGF1, SDF-1α).

To evaluate the quality of the biomaterial, a sample was fixed in formol for hematoxylin-eosin (HE) coloration. The assessment of the decellularization treatment efficacy was evaluated by counting the number of cells in the tissues after HE staining.

5.1.3 Macroscopic Evaluation of Wound Healing

Pictures of legs were taken at days 0, 15, 24 and 34 after implantation.

To quantify the wound closure, the wound area was measured by image analysis using Image J software by two independent operators. The area under the curve was calculated on the wound area measured at each time point between D0 and D34 and were expressed in comparison to the sham group, fixed at 100%.

5.1.4 Microscopic Evaluation of Wound Healing

Legs were dissected to remove the wound tissue and this latest was oriented transversally to have histological slides of the entire thickness of the tissue. Histological slides of 5 μm were prepared and stained with HE for epidermal (op't Veld R C et al, Biomaterials 2018) and dermal scorings (Yates C et al, Biomaterials 2007):

Score epidermal healing in three representative sections of the wound (core and periphery):

0: no migration of epithelial cells,

1: partial migration,

2: complete migration with no/partial keratinization,

3: complete migration with complete keratinization,

4: Advanced hypertrophy.

Score dermal healing in three representative sections of the wound (core and periphery):

0: no healing,

1: inflammatory infiltrate,

2: granulation tissue present-fibroplasias and angiogenesis,

3: collagen deposition replacing granulation tissue >50%,

4: hypertrophic fibrotic response.

In addition, Masson's Trichome coloration was performed for the evaluation of the vascular area by histomorphometry and CD3, CD68 immunostaining for the evaluation of the immune and inflammatory responses. In addition, KU80 staining was performed to identify the presence of human cells after implantation.

5.2. Results

On the 56 rats who received streptozotocin injection, 42 developed hyperglycemia and were selected for the study, while 14 presented low glycemia and developed surgical complications and were therefore excluded from the study.

5.2.1. Macroscopic Evaluation of Wound Healing

Figure 13:
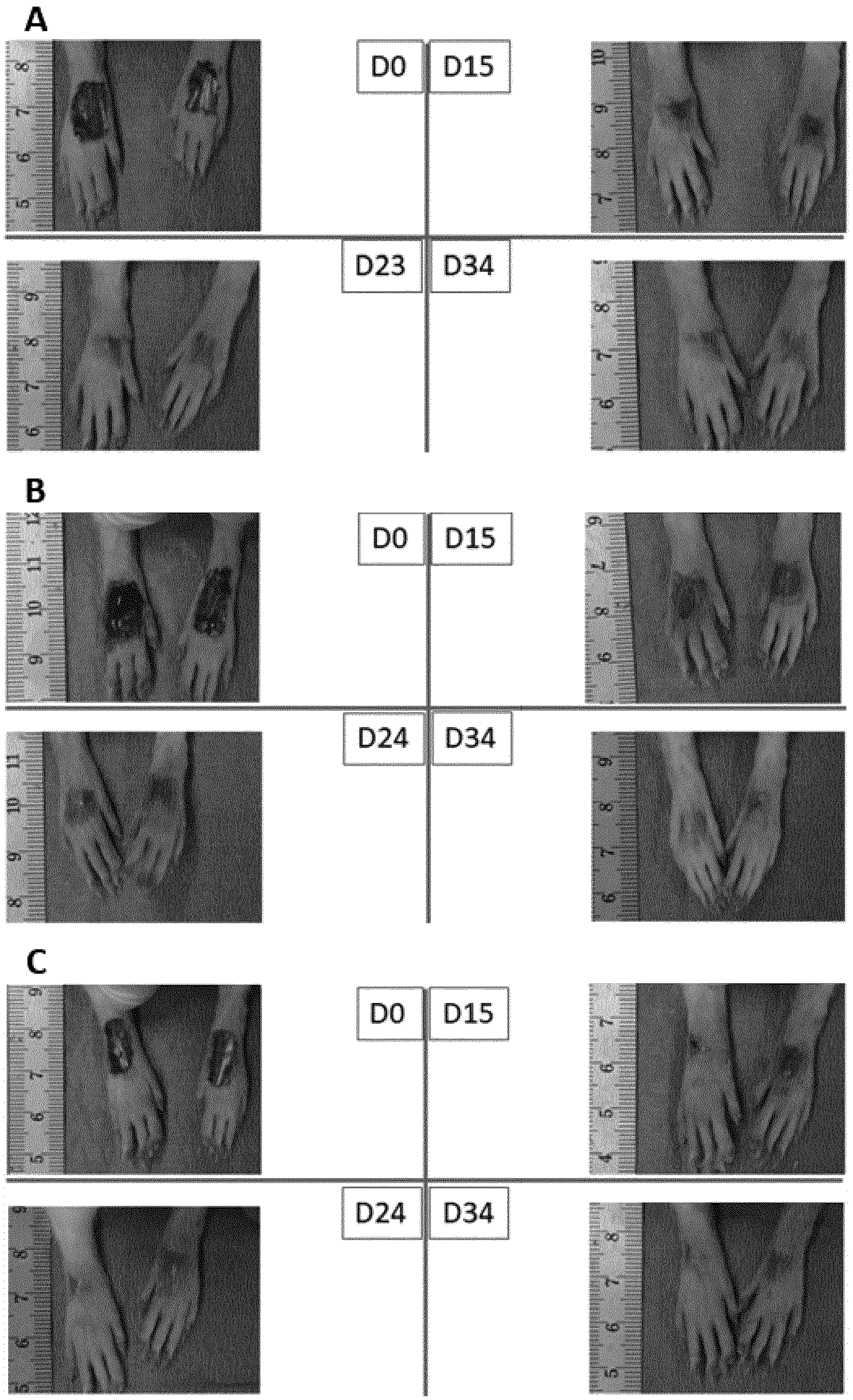
FIGS. 13A-13C are photographs showing wound healing of legs of rats at day 0 (D0), 15 (D15), 23 (D23) and 34 (D34).

Macroscopic pictures of wounds are presented in FIG. 13. A better wound healing can be observed from day 15 after surgery (D15) in the biomaterial group (FIG. 13C) in comparison to other groups (sham control (FIG. 13A) and particles alone, FIG. 13B). This difference is visible for both the ischemic (left limbs) and the non-ischemic wounds (right limbs).

Figure 14:
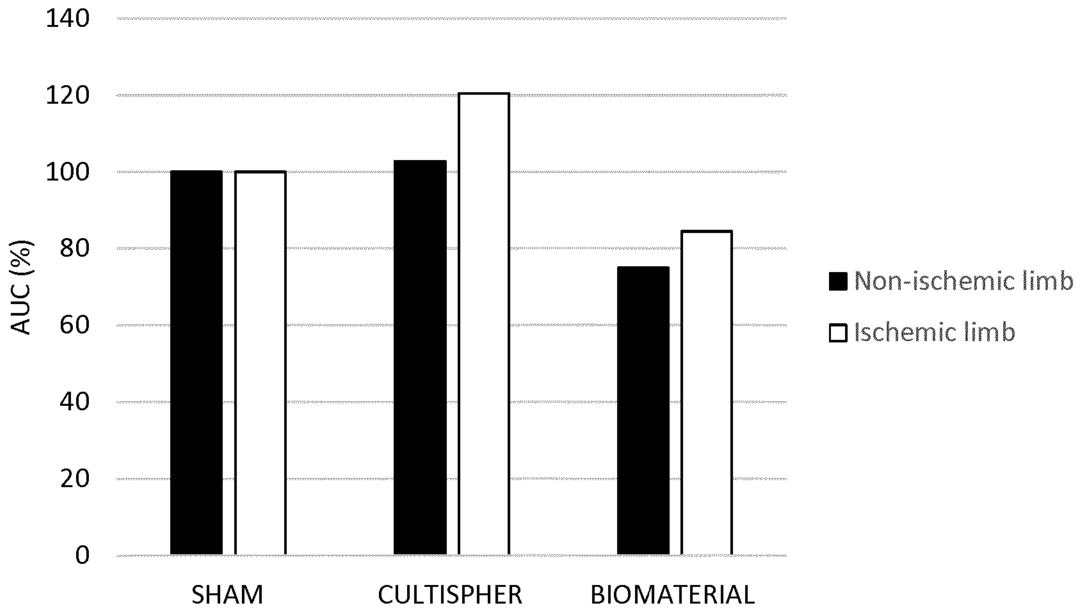
FIG. 14 is a histogram showing area under the curve (AUC) for the wound size in non-ischemic legs (black bars) and ischemic legs (white bars) not treated (sham) or treated with Cultispher S particles alone (Cultispher) or a biomaterial formed with porcine gelatin (Cultispher S) and ASCs at 8 weeks of culture in osteodifferentiation medium (biomaterial), evaluated in comparison with the sham, fixed at 100%.

Results of the areas under the curve for the non-ischemic wound are presented in FIG. 14. Implantation of Cultispher alone showed a decrease of wound healing in comparison to the non-treated animals by 23% respectively. In contrast, a better wound healing (25% was found in the group treated with the biomaterial of the invention.

Figure 15A:
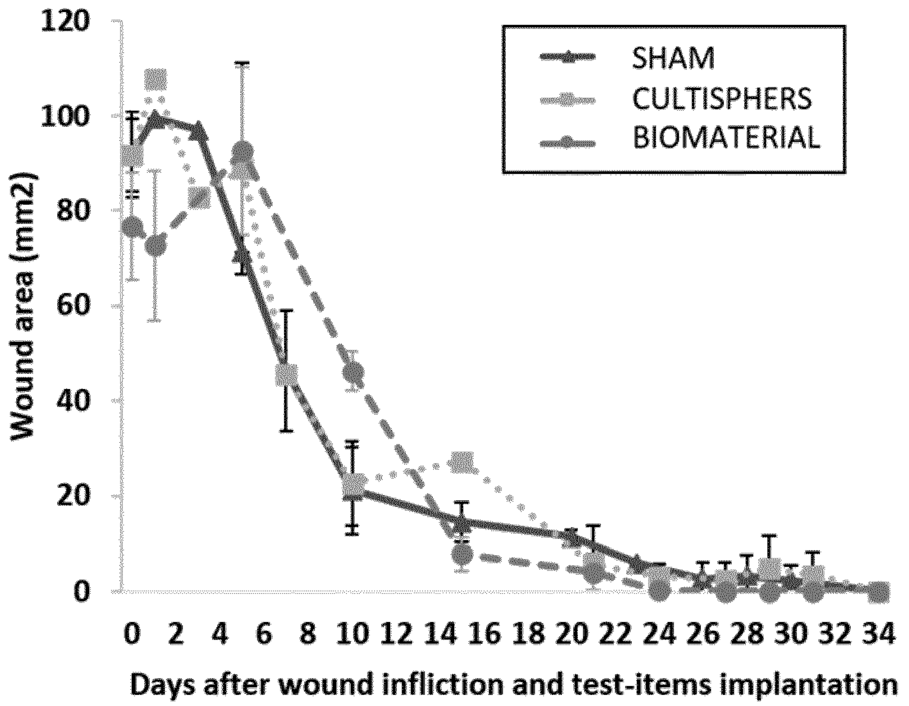
FIGS. 15A-15B are graphs showing wound area in percentage from day 0 to day 34 after treatment with Cultispher S particles alone (squares) or a biomaterial formed with porcine gelatin (Cultispher S) and ASCs at 8 weeks of culture in osteodifferentiation medium (circles), or not treated (sham, triangles).
Figure 15B:
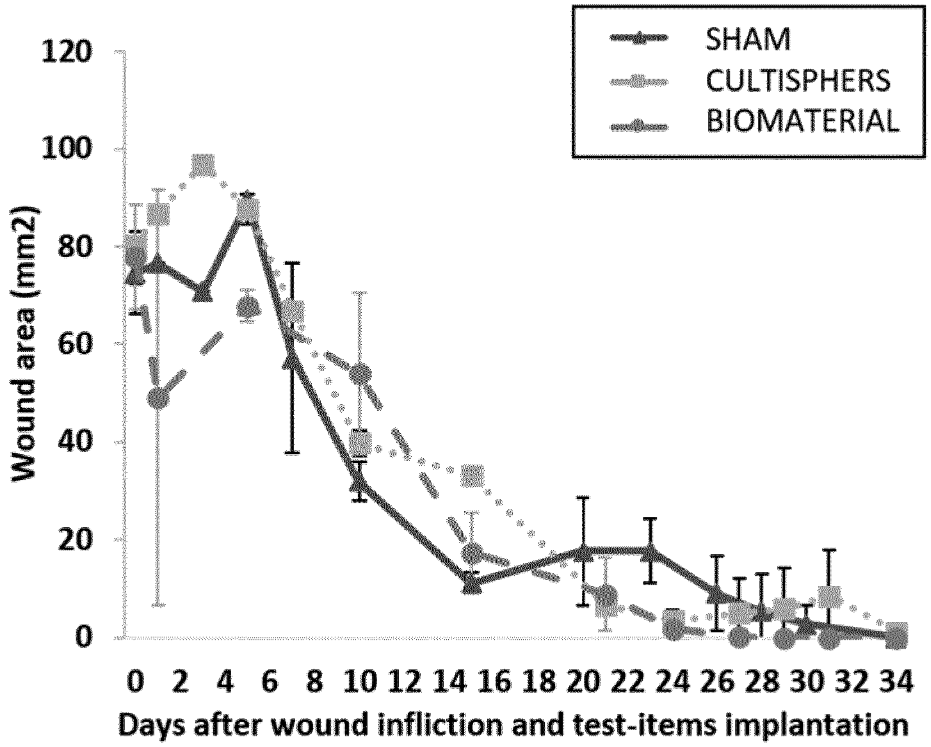
Figure 16A:
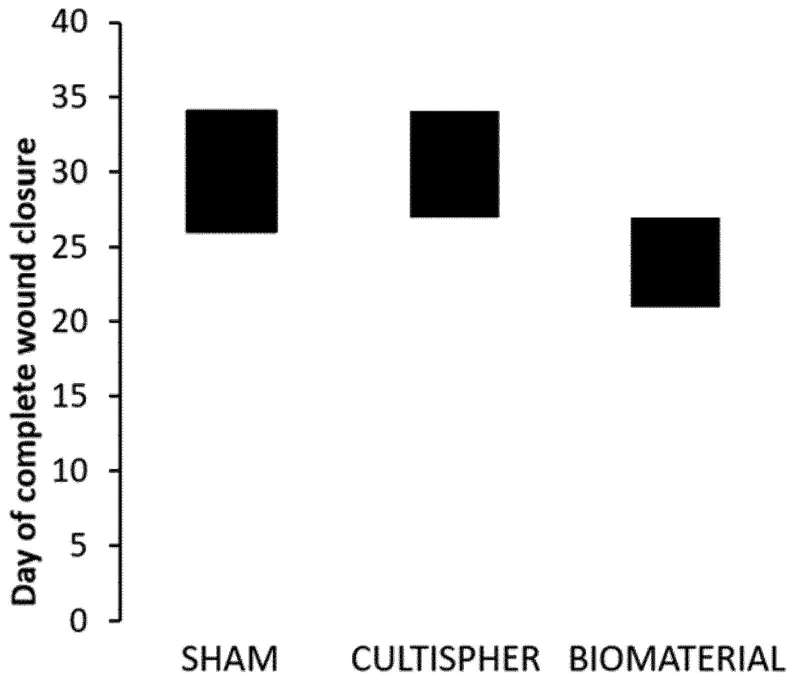
FIGS. 16A-16B are graphs showing days of complete wound closure after no treatment (sham, left), treatment with Cultispher S particles alone (middle) or a biomaterial of the invention (right).
Figure 16B:
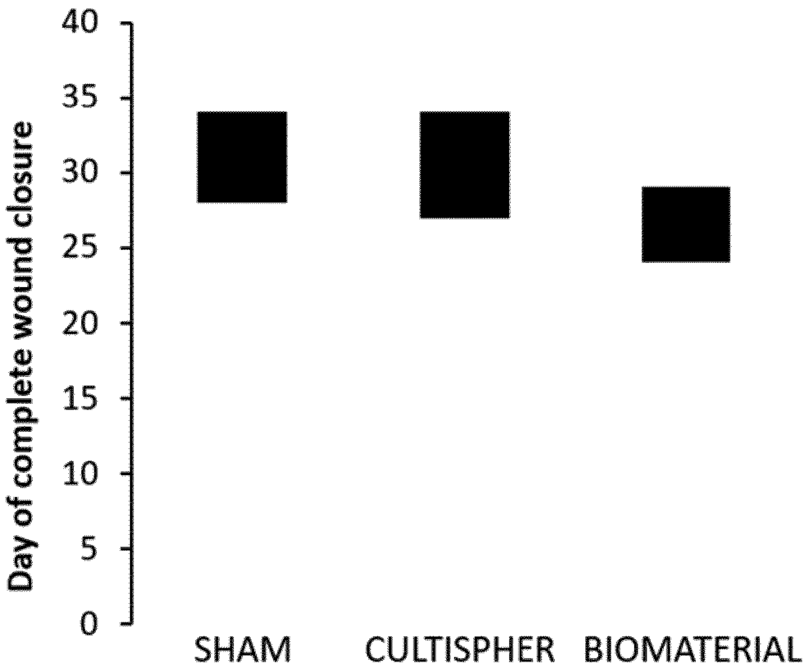

The evolution of wound area for a non-ischemic wound and an ischemic wound between D0 and D34 is presented in FIG. 15 (A and B, respectively). Note that the wounds treated with the biomaterial of the invention present lower non-healed tissues from D21 to D34 in comparison with other groups. Complete closure of the wound is significantly faster when treated with the biomaterial of the invention, in non-ischemic and ischemic conditions (FIGS. 16A and B, respectively).

Figure 17A:
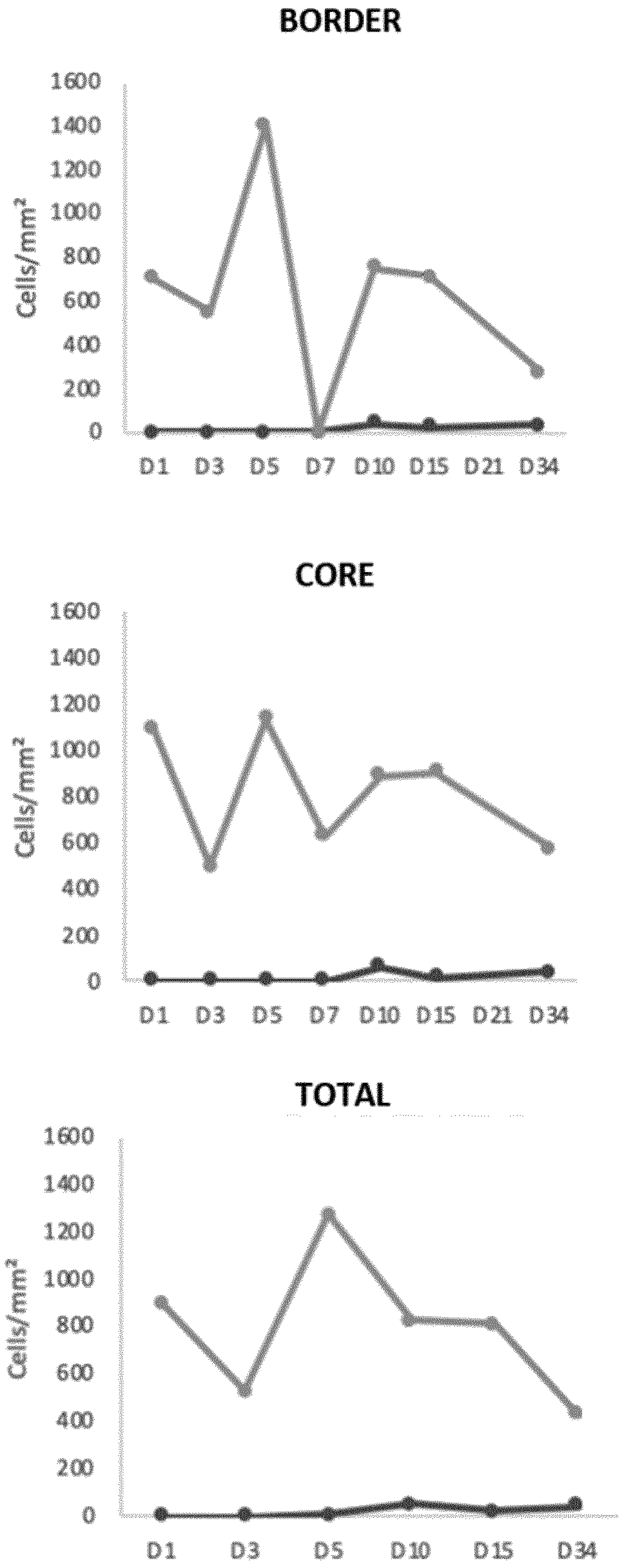
FIGS. 17A-17C are graphs showing number of lymphocytes CD3 (black lines) and macrophages CD68 (gray lines) from day 0 to day 34 after treatment of an ischemic leg.
Figure 17B:
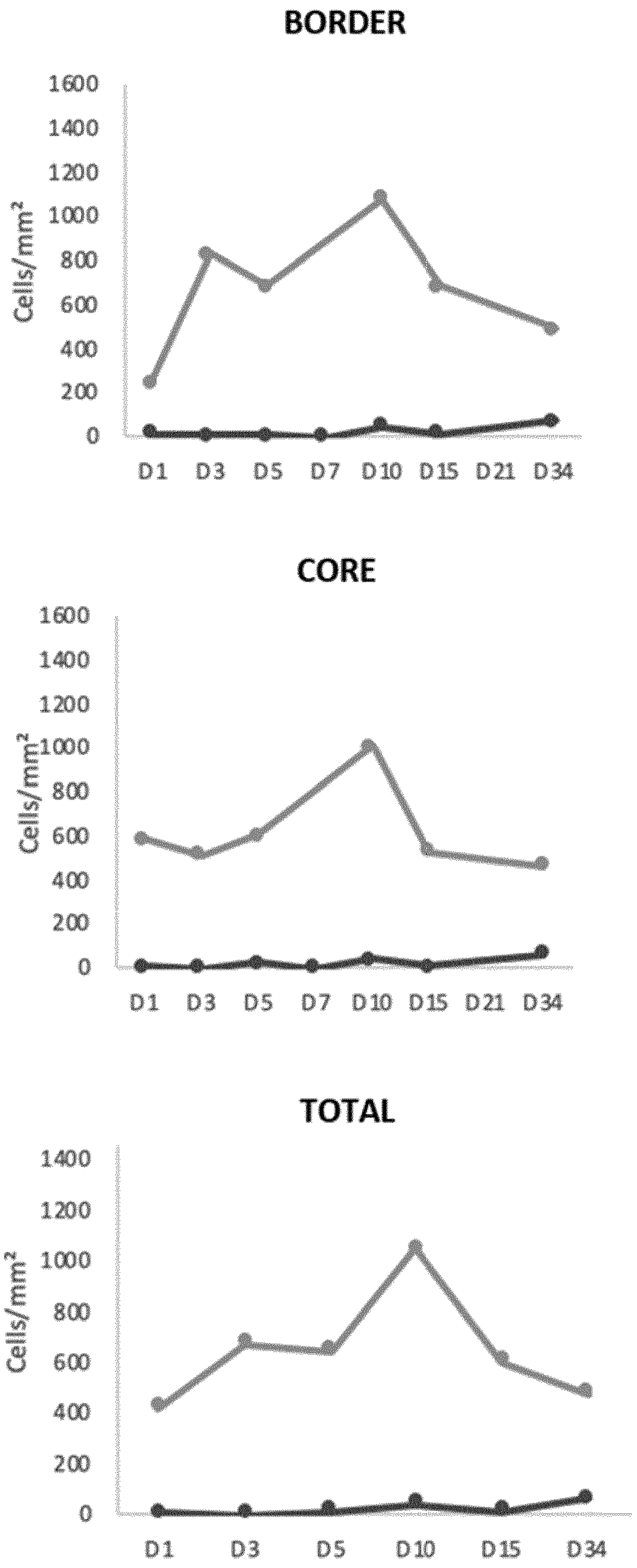
Figure 17C:
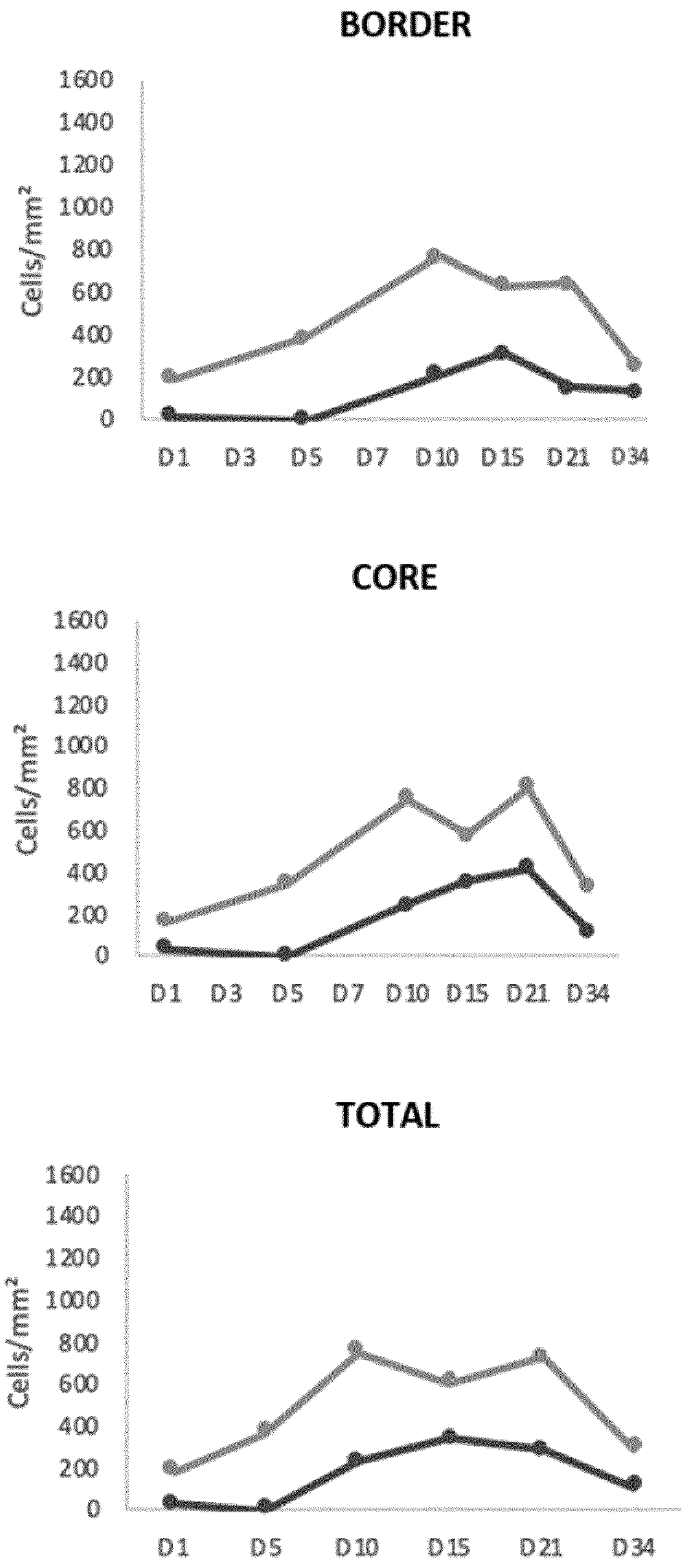

Results of histomorphometry for evaluating inflammatory reaction are presented in FIG. 17. These results show higher lymphocytes CD3 (black line) in border, core and total ischemic wounds treated with the biomaterial of the invention (FIG. 17C) compared to sham control (FIG. 17A) and Cultispher S alone (FIG. 17B). CD3 normally function to destroy infections and malfunctioning cells.

In addition, macrophages CD68 (gray line) reached a peak around D10 (FIG. 17C), like sham control (FIG. 17A) and Cultispher S alone (FIG. 17B). CD68 is characteristic of macrophages which are seen to infest tissue sites and remove cell debris and infections These two observations confirm that implantation of the biomaterial of the invention leads to an increase of the wound closure kinetic by immune elicitation.

Figure 18A:
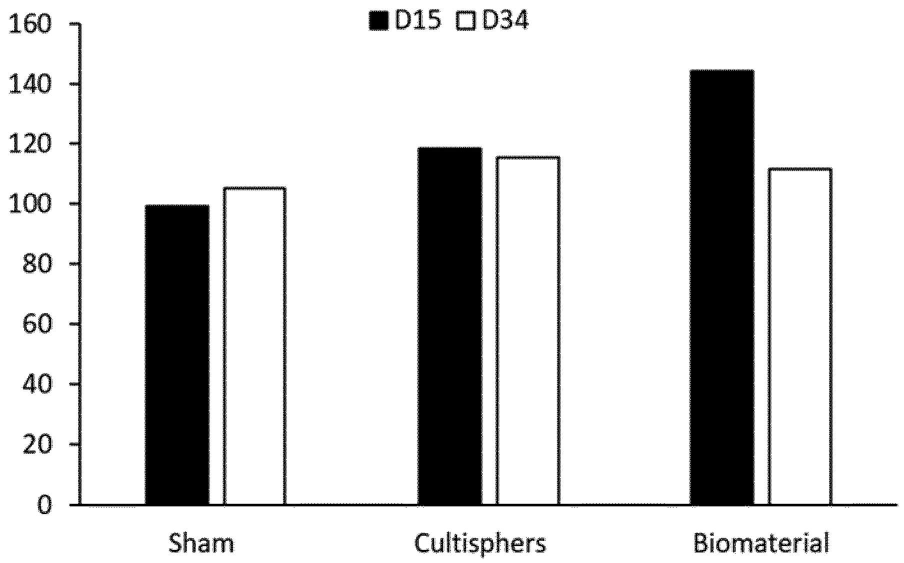
FIGS. 18A-18B are graphs showing the thickness of wound at day 15 and day 34 after no treatment (sham control), after implantation of Cultispher S particles alone (Cultisphers) and after implantation of a biomaterial formed with porcine gelatin (Cultispher S) and ASCs at 8 weeks of culture in osteodifferentiation medium.
Figure 18B:
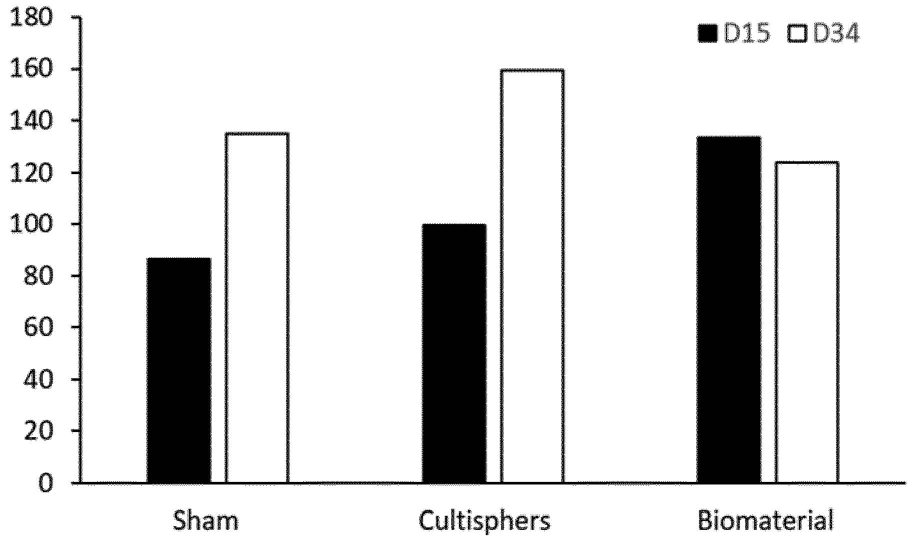

Wound thickness was also assessed (FIG. 18). In an ischemic model (FIG. 18A), the thickness of the wound decreased from D15 to D34 after implantation, showing a retractation. In a non-ischemic model (FIG. 18B), the thickness of the wound slightly decreased from D15 to D34 after implantation, but more importantly did not increase as in the case of sham control and Cultisphers alone. This result highlights the lack of hypertrophy when the biomaterial of the invention is implanted.

5.2.2. Microscopic Evaluation of Wound Healing

Epidermal and dermal scores, evaluated on non-ischemic wounds at each time point, are presented in FIGS. 19A, B, C and D. Faster dermic and epidermic were found for biomaterials of the invention in comparison to other groups.

Example 6: Test of Different Differentiation Media 6.1. Materials and Methods The impact of the differentiation medium on the 3D structure formed was studied. ASCs were cultured with 1.5 $cm^3$ of Cultispher S in different differentiation media for 4 weeks: osteogenic (same as in Example 1), chondrogenic (DMEM, 5% HPL, 100 μg/mL sodium pyruvate, ITS 1×, 40 μg/mL Proline, 10 ng/mL TGF-β1, 1 μM Dexamethazone), keratinogenic (DMEM, 5% HPL, 5 μg/mL insulin, 10 ng/mL KGF, 10 ng/mL hEGF, 0.5 μg/mL hydrocortisone, 1.5 mM CaCl2), and myofibrogenic (DMEM:F12, 100 μg/mL sodium pyruvate, 1×ITS, 1×RPMI 1640 vitamin, 1 ng/mL TGF-β1, 1 μg/mL Glutathione, 0.1 mM MEM). Cultures were maintained for 4 weeks with differentiation medium change every 3-4 days.

Biopsies of tissues at 4 weeks were fixed in formol for hematoxylin-eosin, Masson's Trichrome, and Von Kossa stainings. In addition, tissue-specific stainings were performed (osteocalcin, Alcian Blue, Pankeratin, CD34, α-SMA).

To assess the bioactivity of the tissue formed, biopsies were taken at 4 weeks post-addition of Cultispher for proteins extraction and quantification. The total protein and growth factors contents (VEGF and SDF-1α) were quantified by colorimetry (BCA Protein Assay Kit, ThermoFisher Scientific).

6.2. Results

ASCs and Cultispher S in osteogenic medium serve as positive control for osteogenic differentiation. The formation of a large grippable 3D structure was observed. Histological analysis revealed integration of particles in the cellularized interconnective tissue and an osteocalcine positive staining of the matrix (FIG. 20A).

The culture in chondrogenic medium rapidly (only after a few days) showed the formation of a strength and thick 3D structure, easily grippable and resistant to mechanical forces. Histological analysis revealed integration of particles in the cellularized interconnective tissue and a matrix positive to alcian blue coloration (FIG. 20B).

The myofibrogenic differentiation medium allowed the formation of 3D structures. The structure formed were grippable, but fragile. Again, histological analysis revealed integration of particles in the cellularized interconnective tissue and α-SMA positive staining of the matrix (FIG. 20C).

ASCs and particles in keratinogenic medium formed a large, plane and thin 3D structure. This latest was very fragile and difficult to handle (FIG. 20D).

(Table 6).

TABLE 6

Characteristics of the structures formed in the differentiation media tested

| Differentiation medium | 3D structure | Grippable | Solidity | Interconnective tissue |
|---|---|---|---|---|
| Osteogenic | + | + | +/− | + |
| Chondrogenic | + | + | + | + |
| Myofibrogenic | + | +/− | +/− | + |
| Keratinogenic | + | +/− | − | + |

Therefore, a 3D structure was observed in all the samples of biomaterial formed with ASCs and gelatin, with all the differentiation media tested.

The invention claimed is:

1. A scaffold-free biomaterial having a multi-dimensional structure comprising differentiated adipose-derived stem cells (ASCs), an extracellular matrix and gelatin, wherein the multi-dimensional biomaterial is obtainable by a method comprising the steps of:

adipose-derived stem cells (ASCs) proliferation,

ASCs osteogenic differentiation, and multi-dimensional induction, or 3D induction, wherein the induction is through the addition of gelatin particles.

2. The biomaterial according to claim 1, wherein said gelatin is porcine gelatin.

3. The biomaterial according to claim 1, wherein said particles have a mean diameter a. ranging from about 50 μm to about 1000 μm, or b. ranging from about 75 μm to about 750 μm, or c. ranging from about 100 μm to about 500 μm.

4. The biomaterial according to claim 1, wherein said biomaterial is three-dimensional.

5. The biomaterial according to claim 1, wherein said ASCs are differentiated into osteoblasts.

* * * * *